(12) United States Patent
Herweck et al.

(10) Patent No.: US 9,050,442 B2
(45) Date of Patent: Jun. 9, 2015

(54) EXPANDABLE FLUOROPOLYMER DEVICE FOR DELIVERY OF THERAPEUTIC AGENTS AND METHOD OF MAKING

(75) Inventors: Steve A. Herweck, Nashua, NH (US); Peter H. Gingras, Windham, NH (US); Paul Martakos, Pelham, NH (US); Theodore Karwoski, Hollis, NH (US)

(73) Assignee: Atrium Medical Corporation, Merrimack, NH (US)

( * ) Notice: Subject to any disclaimer, the term of this patent is extended or adjusted under 35 U.S.C. 154(b) by 722 days.

(21) Appl. No.: 12/820,938

(22) Filed: Jun. 22, 2010

(65) Prior Publication Data

US 2011/0118703 A1 May 19, 2011

Related U.S. Application Data

(60) Continuation of application No. 11/068,680, filed on Feb. 28, 2005, now Pat. No. 7,740,793, which is a division of application No. 09/411,797, filed on Oct. 1, 1999, now Pat. No. 6,955,661.

(60) Provisional application No. 60/117,152, filed on Jan. 25, 1999.

(51) Int. Cl.
*A61M 31/00* (2006.01)
*A61M 25/10* (2013.01)
(Continued)

(52) U.S. Cl.
CPC .......... *A61M 25/1029* (2013.01); *A61L 29/041* (2013.01); *A61M 25/10* (2013.01);
(Continued)

(58) Field of Classification Search
CPC .............. A51M 2025/105; A61M 2025/1086; A61M 25/10

USPC ................. 604/103.01, 103.06, 509
See application file for complete search history.

(56) References Cited

U.S. PATENT DOCUMENTS

| 3,635,223 | A | 1/1972 | Klieman |
| 3,888,249 | A | 6/1975 | Spencer |

(Continued)

FOREIGN PATENT DOCUMENTS

| CA | 2262484 A1 | 2/1998 |
| DE | 10115740 | 10/2002 |

(Continued)

OTHER PUBLICATIONS

European Supplementary Search Report for European Application 08746780.9, dated Nov. 9, 2012.

(Continued)

*Primary Examiner* — Emily Schmidt

(57) ABSTRACT

A method of making a radially expandable fluid delivery device includes providing a tube of biocompatible fluoropolymer material with a predetermined porosity based on an extrusion and expansion forming process, applying a radial expansion force to the tube expanding the tube to a predetermined diameter dimension, and removing the radial expansion force. The tube is radially inelastic while sufficiently pliable to be collapsible and inflatable from a collapsed configuration to an expanded configuration upon introduction of an inflation force, such that the expanded configuration occurs upon inflation to the predetermined diameter dimension. The fluid delivery device is constructed of a microporous, biocompatible fluoropolymer material having a microstructure that can provide a controlled, uniform, low-velocity fluid distribution through the walls of the fluid delivery device to effectively deliver fluid to the treatment site without damaging tissue proximate the walls of the device.

24 Claims, 11 Drawing Sheets

(51) Int. Cl.

| | | |
|---|---|---|
| *A61L 29/04* | (2006.01) | |
| *B29C 55/24* | (2006.01) | |
| *A61M 25/00* | (2006.01) | |
| *B29C 47/00* | (2006.01) | |
| *B29C 49/46* | (2006.01) | |
| *B29K 27/18* | (2006.01) | |
| *B29L 22/02* | (2006.01) | |
| *B29L 31/00* | (2006.01) | |

(52) U.S. Cl.
CPC .. *A61M2025/0057* (2013.01); *A61M 2025/105* (2013.01); *A61M 2025/1075* (2013.01); *B29C 47/00* (2013.01); *B29C 47/0023* (2013.01); *B29C 55/24* (2013.01); *B29C 2049/465* (2013.01); *B29K 2027/18* (2013.01); *B29L 2022/022* (2013.01); *B29L 2031/753* (2013.01); *B32B 2305/026* (2013.01)

(56) References Cited

U.S. PATENT DOCUMENTS

| | | |
|---|---|---|
| 3,901,232 A | 8/1975 | Michaels et al. |
| 3,981,299 A | 9/1976 | Murray |
| 4,030,503 A | 6/1977 | Clark, III |
| 4,229,838 A | 10/1980 | Mano |
| 4,292,974 A | 10/1981 | Fogarty et al. |
| 4,323,071 A | 4/1982 | Simpson et al. |
| 4,327,721 A | 5/1982 | Goldin et al. |
| 4,338,942 A | 7/1982 | Fogarty |
| 4,364,392 A * | 12/1982 | Strother et al. ............... 606/195 |
| 4,406,656 A | 9/1983 | Hattler et al. |
| 4,417,576 A | 11/1983 | Baran |
| 4,423,725 A | 1/1984 | Baran et al. |
| 4,437,856 A | 3/1984 | Valli |
| 4,490,421 A | 12/1984 | Levy |
| 4,573,966 A | 3/1986 | Weikl et al. |
| 4,581,140 A | 4/1986 | Manabe et al. |
| 4,636,195 A | 1/1987 | Wolinsky |
| 4,637,396 A | 1/1987 | Cook |
| 4,650,466 A | 3/1987 | Luther |
| 4,661,094 A | 4/1987 | Simpson |
| 4,692,200 A | 9/1987 | Powell |
| 4,693,243 A | 9/1987 | Buras |
| 4,702,252 A | 10/1987 | Brooks et al. |
| 4,711,251 A | 12/1987 | Stokes |
| 4,713,070 A | 12/1987 | Mano |
| 4,714,460 A | 12/1987 | Calderon |
| 4,714,461 A | 12/1987 | Gabel |
| 4,721,507 A | 1/1988 | Chin |
| 4,744,366 A | 5/1988 | Jang |
| 4,762,129 A | 8/1988 | Bonzel |
| 4,762,130 A | 8/1988 | Fogarty et al. |
| 4,775,371 A | 10/1988 | Mueller |
| 4,799,479 A | 1/1989 | Spears |
| 4,820,349 A | 4/1989 | Saab |
| 4,824,436 A | 4/1989 | Wolinsky |
| 4,832,688 A | 5/1989 | Sagae et al. |
| RE32,983 E | 7/1989 | Levy |
| 4,850,969 A | 7/1989 | Jackson |
| 4,877,031 A | 10/1989 | Conway et al. |
| 4,935,190 A | 6/1990 | Tennerstedt |
| 4,941,877 A | 7/1990 | Montano, Jr. |
| 4,957,669 A | 9/1990 | Primm |
| 4,968,306 A | 11/1990 | Huss et al. |
| 4,968,307 A | 11/1990 | Dake et al. |
| 4,994,033 A | 2/1991 | Shockey et al. |
| 5,015,232 A | 5/1991 | Maglinte |
| 5,021,044 A | 6/1991 | Sharkawy |
| 5,034,082 A | 7/1991 | Nolan |
| 5,041,089 A | 8/1991 | Mueller et al. |
| 5,041,090 A | 8/1991 | Scheglov et al. |
| 5,041,125 A | 8/1991 | Montano, Jr. |
| 5,047,028 A | 9/1991 | Qian |
| 5,049,132 A | 9/1991 | Shaffer et al. |
| 5,071,424 A | 12/1991 | Reger |
| 5,071,609 A | 12/1991 | Tu et al. ........................ 264/119 |
| 5,087,244 A | 2/1992 | Wolinsky et al. |
| 5,087,246 A | 2/1992 | Smith |
| 5,087,247 A | 2/1992 | Horn et al. |
| 5,087,394 A | 2/1992 | Keith |
| 5,098,381 A | 3/1992 | Schneider |
| 5,100,383 A | 3/1992 | Lichtenstein |
| 5,102,402 A | 4/1992 | Dror et al. |
| 5,112,305 A | 5/1992 | Barath et al. |
| 5,112,347 A | 5/1992 | Taheri |
| 5,156,610 A | 10/1992 | Reger |
| 5,176,638 A | 1/1993 | Don Michael |
| 5,192,290 A | 3/1993 | Hilal |
| 5,199,951 A | 4/1993 | Spears |
| 5,211,651 A | 5/1993 | Reger et al. |
| 5,213,576 A | 5/1993 | Abiuso et al. |
| 5,232,444 A | 8/1993 | Just et al. |
| 5,236,413 A | 8/1993 | Feiring |
| 5,236,659 A | 8/1993 | Pinchuk et al. |
| 5,254,089 A | 10/1993 | Wang |
| 5,257,974 A | 11/1993 | Cox |
| 5,267,985 A | 12/1993 | Shimada et al. |
| 5,269,755 A | 12/1993 | Bodicky |
| 5,279,565 A | 1/1994 | Klein et al. |
| 5,282,484 A | 2/1994 | Reger |
| 5,282,785 A | 2/1994 | Shapland et al. |
| 5,286,254 A | 2/1994 | Shapland et al. |
| 5,295,962 A | 3/1994 | Crocker et al. |
| 5,304,121 A | 4/1994 | Sahatjian |
| 5,304,340 A | 4/1994 | Downey et al. |
| 5,306,250 A | 4/1994 | March et al. |
| 5,318,531 A | 6/1994 | Leone |
| 5,336,178 A | 8/1994 | Kaplan et al. |
| 5,344,402 A | 9/1994 | Crocker |
| 5,364,356 A | 11/1994 | Hofling |
| 5,368,566 A | 11/1994 | Crocker |
| 5,370,614 A | 12/1994 | Amundson et al. |
| 5,397,307 A | 3/1995 | Goodin |
| 5,405,472 A | 4/1995 | Leone |
| 5,415,636 A | 5/1995 | Forman |
| 5,421,826 A | 6/1995 | Crocker et al. |
| 5,433,909 A | 7/1995 | Martakos et al. .......... 264/209.1 |
| 5,447,940 A | 9/1995 | Harvey et al. |
| 5,456,661 A | 10/1995 | Narciso |
| 5,456,666 A | 10/1995 | Campbell et al. |
| 5,456,667 A | 10/1995 | Ham et al. |
| 5,458,568 A | 10/1995 | Racchini et al. |
| 5,458,572 A | 10/1995 | Campbell et al. |
| 5,474,824 A | 12/1995 | Martakos et al. |
| 5,490,839 A | 2/1996 | Wang et al. |
| 5,498,238 A | 3/1996 | Shapland et al. |
| 5,499,971 A | 3/1996 | Shapland et al. |
| 5,499,995 A | 3/1996 | Teirstein |
| 5,500,180 A | 3/1996 | Anderson et al. |
| 5,500,181 A | 3/1996 | Wang et al. |
| 5,509,899 A | 4/1996 | Fan et al. |
| 5,512,051 A | 4/1996 | Wang et al. |
| 5,514,092 A | 5/1996 | Forman et al. |
| 5,522,800 A | 6/1996 | Crocker |
| 5,533,516 A | 7/1996 | Sahatjian |
| 5,569,198 A | 10/1996 | Racchini |
| 5,628,730 A | 5/1997 | Shapland et al. |
| 5,634,899 A | 6/1997 | Shapland et al. |
| 5,637,113 A | 6/1997 | Tartaglia et al. |
| 5,653,689 A | 8/1997 | Buelna et al. |
| 5,693,014 A | 12/1997 | Abele et al. |
| 5,700,286 A | 12/1997 | Tartaglia et al. |
| 5,707,385 A | 1/1998 | Williams |
| 5,709,653 A | 1/1998 | Leone |
| 5,713,853 A | 2/1998 | Clark et al. |
| 5,735,897 A | 4/1998 | Buirge |
| 5,749,845 A | 5/1998 | Hildebrand et al. |
| 5,752,934 A | 5/1998 | Campbell et al. |
| 5,772,632 A | 6/1998 | Forman |
| 5,782,797 A | 7/1998 | Schweich, Jr. et al. |
| 5,800,392 A | 9/1998 | Racchini |
| 5,807,306 A | 9/1998 | Shapland et al. |
| 5,810,767 A | 9/1998 | Klein |

(56) References Cited

U.S. PATENT DOCUMENTS

| | | | |
|---|---|---|---|
| 5,823,996 A | 10/1998 | Sparks | |
| 5,833,659 A | 11/1998 | Kranyls | |
| 5,843,033 A | 12/1998 | Ropiak | |
| 5,843,069 A | 12/1998 | Butler et al. | |
| 5,860,954 A | 1/1999 | Ropiak | |
| 5,865,787 A | 2/1999 | Shapland et al. | |
| 5,868,704 A | 2/1999 | Campbell et al. | |
| 5,868,719 A | 2/1999 | Tsukernik | |
| 5,871,468 A | 2/1999 | Kramer et al. | |
| 5,882,335 A | 3/1999 | Leone et al. | |
| 5,902,266 A | 5/1999 | Leone et al. | |
| 5,928,193 A | 7/1999 | Campbell | |
| 5,947,977 A | 9/1999 | Slepian et al. | |
| 5,948,345 A | 9/1999 | Patel et al. | |
| 6,010,480 A | 1/2000 | Abele et al. | |
| 6,013,055 A | 1/2000 | Bampos et al. | |
| 6,015,844 A | 1/2000 | Harvey et al. | |
| 6,033,380 A | 3/2000 | Butaric et al. | |
| 6,048,332 A | 4/2000 | Duffy et al. | |
| 6,075,180 A | 6/2000 | Sharber et al. | |
| 6,120,477 A | 9/2000 | Campbell et al. | |
| 6,120,789 A | 9/2000 | Dunn | |
| 6,135,982 A | 10/2000 | Campbell | |
| 6,139,572 A | 10/2000 | Campbell et al. | |
| 6,146,358 A | 11/2000 | Rowe | |
| 6,156,254 A | 12/2000 | Andrews et al. | |
| 6,159,227 A | 12/2000 | Di Caprio et al. | |
| 6,200,985 B1 | 3/2001 | Cottens et al. | |
| 6,203,735 B1 | 3/2001 | Edwin et al. | 264/127 |
| 6,206,916 B1 | 3/2001 | Furst | |
| 6,231,600 B1 | 5/2001 | Zhong | |
| 6,270,523 B1 | 8/2001 | Herweck et al. | 623/1.13 |
| 6,287,285 B1 | 9/2001 | Michal et al. | |
| 6,296,657 B1 | 10/2001 | Brucker | |
| 6,299,604 B1 | 10/2001 | Ragheb et al. | |
| 6,355,063 B1 | 3/2002 | Calcote | |
| 6,358,227 B1 | 3/2002 | Ferrera et al. | |
| 6,358,556 B1 | 3/2002 | Ding et al. | |
| 6,364,856 B1 | 4/2002 | Ding et al. | |
| 6,364,893 B1 | 4/2002 | Sahatjian et al. | |
| 6,364,903 B2 | 4/2002 | Tseng et al. | |
| 6,369,039 B1 | 4/2002 | Palasis et al. | |
| 6,375,637 B1 | 4/2002 | Campbell et al. | |
| 6,386,626 B1 | 5/2002 | Makino et al. | |
| 6,395,208 B1 | 5/2002 | Herweck et al. | 264/127 |
| 6,451,373 B1 | 9/2002 | Hossainy et al. | |
| 6,463,323 B1 | 10/2002 | Conrad-Vlasak et al. | |
| 6,491,938 B2 | 12/2002 | Kunz | |
| 6,500,174 B1 | 12/2002 | Maguire et al. | |
| 6,534,693 B2 | 3/2003 | Fischell et al. | |
| 6,541,116 B2 | 4/2003 | Michal et al. | |
| 6,544,223 B1 | 4/2003 | Kokish | |
| 6,544,224 B1 | 4/2003 | Steese-Bradley et al. | |
| 6,610,035 B2 | 8/2003 | Yang et al. | |
| 6,616,650 B1 | 9/2003 | Rowe | |
| 6,641,611 B2 | 11/2003 | Jayaraman | |
| 6,730,016 B1 | 5/2004 | Cox et al. | |
| 6,730,064 B2 | 5/2004 | Ragheb et al. | |
| 6,758,847 B2 | 7/2004 | Maguire | |
| 6,764,509 B2 | 7/2004 | Chinn et al. | |
| 6,808,536 B2 | 10/2004 | Wright et al. | |
| 6,833,004 B2 | 12/2004 | Ishii et al. | |
| 6,899,729 B1 | 5/2005 | Cox et al. | |
| 6,902,522 B1 | 6/2005 | Walsh et al. | |
| 6,918,927 B2 | 7/2005 | Bates et al. | |
| 6,955,661 B1 | 10/2005 | Herweck et al. | |
| 7,090,655 B2 | 8/2006 | Barry | |
| 7,311,980 B1 | 12/2007 | Hossainy et al. | |
| 7,491,188 B2 | 2/2009 | Holman et al. | |
| 7,572,245 B2 | 8/2009 | Herweck et al. | |
| 7,637,886 B2 | 12/2009 | Herweck et al. | |
| 7,740,793 B2 | 6/2010 | Herweck et al. | |
| 7,947,015 B2 | 5/2011 | Herweck et al. | |
| 8,021,331 B2 | 9/2011 | Herweck et al. | |
| 8,052,744 B2 | 11/2011 | Girton | |
| 8,211,055 B2 | 7/2012 | Christiansen | |
| 8,308,684 B2 | 11/2012 | Herweck et al. | |
| 2001/0014717 A1 | 8/2001 | Hossany | |
| 2002/0082679 A1 | 6/2002 | Sirhan et al. | |
| 2002/0091435 A1 | 7/2002 | Campbell | |
| 2002/0122903 A1 | 9/2002 | Ferrera et al. | |
| 2002/0198521 A1 | 12/2002 | Maguire | |
| 2003/0083740 A1 | 5/2003 | Pathak | |
| 2003/0152609 A1 | 8/2003 | Fischell et al. | |
| 2003/0204168 A1 | 10/2003 | Bosma et al. | |
| 2004/0006296 A1 | 1/2004 | Fischell et al. | |
| 2004/0013704 A1 | 1/2004 | Kabra et al. | |
| 2004/0018228 A1 | 1/2004 | Fischell et al. | |
| 2004/0039441 A1 | 2/2004 | Rowland et al. | |
| 2004/0071756 A1 | 4/2004 | Fischell et al. | |
| 2004/0073284 A1 | 4/2004 | Bates et al. | |
| 2004/0082965 A1 | 4/2004 | Beckham | |
| 2004/0102758 A1 | 5/2004 | Davilia et al. | |
| 2004/0137066 A1 | 7/2004 | Jayaraman | |
| 2004/0167572 A1 | 8/2004 | Roth et al. | |
| 2004/0230176 A1 | 11/2004 | Shanahan et al. | |
| 2004/0235762 A1 | 11/2004 | Abel et al. | |
| 2004/0236278 A1 | 11/2004 | Herweck et al. | |
| 2005/0084514 A1 | 4/2005 | Shebuski et al. | |
| 2005/0101522 A1 | 5/2005 | Speck et al. | |
| 2005/0106206 A1 | 5/2005 | Herweck et al. | |
| 2005/0113687 A1 | 5/2005 | Herweck et al. | |
| 2005/0154416 A1 | 7/2005 | Herweck et al. | |
| 2005/0158361 A1 | 7/2005 | Dhondt et al. | |
| 2005/0159809 A1 | 7/2005 | Hezi-Yamit et al. | |
| 2005/0182485 A1 | 8/2005 | Falotico et al. | |
| 2005/0187376 A1 | 8/2005 | Pacetti et al. | |
| 2005/0232971 A1 | 10/2005 | Hossainy et al. | |
| 2006/0008501 A1 | 1/2006 | Dhont et al. | |
| 2006/0036311 A1 | 2/2006 | Nakayama et al. | |
| 2010/0209473 A1 | 8/2010 | Dhont et al. | |
| 2011/0160575 A1 | 6/2011 | Beyar et al. | |
| 2013/0035637 A1 | 2/2013 | Herweck et al. | |

FOREIGN PATENT DOCUMENTS

| | | |
|---|---|---|
| EP | 0293090 | 11/1988 |
| EP | 0372088 | 6/1990 |
| EP | 383429 | 8/1990 |
| EP | 0531117 | 1/1997 |
| EP | 788774 | 8/1997 |
| EP | 835673 | 4/1998 |
| EP | 1148899 | 10/2001 |
| EP | 1557183 A1 | 7/2005 |
| JP | 5305146 | 11/1993 |
| WO | WO 87/06846 | 11/1987 |
| WO | WO 89/12478 | 12/1989 |
| WO | WO 90/01969 | 3/1990 |
| WO | WO 91/08790 | 6/1991 |
| WO | WO 91/19529 | 12/1991 |
| WO | WO 94/05369 | 3/1994 |
| WO | WO 94/21320 | 9/1994 |
| WO | WO 97/10871 | 3/1997 |
| WO | WO 97/17889 | 5/1997 |
| WO | WO 97/31590 | 9/1997 |
| WO | 98/05377 A1 | 2/1998 |
| WO | WO 98/26731 | 6/1998 |
| WO | WO 98/31415 | 7/1998 |
| WO | WO 98/33638 | 8/1998 |
| WO | WO 99/16500 | 4/1999 |
| WO | WO99/27989 | 6/1999 |
| WO | WO 00/12147 | 3/2000 |
| WO | WO 00/40278 | 7/2000 |
| WO | WO 00/43051 | 7/2000 |
| WO | 2000/057815 A1 | 10/2000 |
| WO | WO 01/15764 | 3/2001 |
| WO | WO 01/24866 | 4/2001 |
| WO | WO 01/80937 | 11/2001 |
| WO | WO 02/22199 | 3/2002 |
| WO | WO 02/26279 | 4/2002 |
| WO | WO 02/076509 | 10/2002 |
| WO | WO 03/028622 | 4/2003 |
| WO | WO 03/039612 | 5/2003 |
| WO | WO 2004/006976 | 1/2004 |

(56) References Cited

FOREIGN PATENT DOCUMENTS

| WO | WO 2004/028582 | 4/2004 |
|---|---|---|
| WO | WO 2004/028610 | 4/2004 |
| WO | WO 2005/027996 | 3/2005 |
| WO | WO 2007/047116 | 4/2007 |
| WO | WO 2008/144162 | 11/2008 |

OTHER PUBLICATIONS

European Supplementary Search Report for European Application 04784410.5, dated Oct. 31, 2011.
Hwang, et al., "Physiological transport forces govern drug distribution for stent-based delivery", *Circulation*, 104(5): 600-605 (2001).
Lambert, C.R. et al., "Local drug delivery catheters: functional comparison of porous and microporous designs," *Current Science*, 4(5):469-475 (1993).
Oberhoff, et al., "Local and systemic delivery of low molecular weight heparin following PTCA: acute results and 6-month follow-up of the initial clinical experience with the porous balloon (PILOT-study)", Preliminary Investigation of Local Therapy Using Porous PTCA Balloons, *Cathet. Cardiovasc. Diagn.*, 44(3): 267-274 (1998).
Wolinsky, H., "Historical perspective," *Semin Intervent Cardiol* 1:3-7 (1996).
International Search Report for Application No. PCT/US00/02191, dated Jun. 21, 2000.
European Supplementary Search Report for European Application EP 0478411, dated Mar. 30, 2011.
Non-Final Office Action for U.S. Appl. No. 10/942,764 (listed on SB-08 as U.S. Patent No. 7,572,245), mailed Oct. 2, 2006.
Non-Final Office Action for U.S. Appl. No. 10/942,764 (listed on SB-08 as U.S. Patent No. 7,572,245), mailed Jun. 30, 2008.
Notice of Allowance for U.S. Appl. No. 10/942,764 (listed on SB-08 as U.S. Patent No. 7,572,245), mailed Feb. 25, 2009.
Non-Final Office Action for U.S. Appl. No. 10/131,396 (listed on SB-08 as U.S. Patent No. 7,637,886), mailed Dec. 3, 2004.
Final Office Action for U.S. Appl. No. 10/131,396 (listed on SB-08 as U.S. Patent No. 7,637,886), mailed Oct. 6, 2005.
Advisory Action for U.S. Appl. No. 10/131,396 (listed on SB-08 as U.S. patent No. 7,637,886), mailed Feb. 28, 2006.
Non-Final Office Action for U.S. Appl. No. 10/131,396 (listed on SB-08 as U.S. Patent No. 7,637,886), mailed Jun. 20, 2006.
Final Office Action for U.S. Appl. No. 10/131,396 (listed on SB-08 as U.S. Patent No. 7,637,886), mailed Nov. 27, 2006.
Advisory Action for U.S. Appl. No. 10/131,396 (listed on SB-08 as U.S. patent No. 7,637,886), mailed Apr. 17, 2007.
Non-Final Office Action for U.S. Appl. No. 10/131,396 (listed on SB-08 as U.S. Patent No. 7,637,886), mailed Aug. 9, 2007.
Final Office Action for U.S. Appl. No. 10/131,396 (listed on SB-08 as U.S. Patent No. 7,637,886), mailed Jan. 1, 2008.
Final Office Action for U.S. Appl. No. 10/131,396 (listed on SB-08 as U.S. Patent No. 7,637,886), mailed Nov. 14, 2008.
Notice of Allowance for U.S. Appl. No. 10/131,396 (listed on SB-08 as U.S. Patent No. 7,637,886), mailed Aug. 20, 2009.
Non-Final Office Action for U.S. Appl. No. 11/804,478 (listed on SB-08 as U.S. Patent No. 7,947,015), mailed Apr. 15, 2009.
Final Office Action for U.S. Appl. No. 11/804,478 (listed on SB-08 as U.S. Patent No. 7,947,015), mailed Dec. 30, 2009.
Notice of Allowance for U.S. Appl. No. 11/804,478 (listed on SB-08 as U.S. Patent No. 7,947,015), mailed Jan. 20, 2011.
Final Office Action for U.S. Appl. No. 09/411,797 (listed on SB-08 as U.S. Patent No. 6,955,661), mailed Mar. 27, 2002.
Non-Final Office Action for U.S. Appl. No. 09/411,797 (listed on SB-08 as U.S. Patent No. 6,955,661), mailed Jun. 20, 2001.
Advisory Action for U.S. Appl. No. 09/411,797 (listed on SB-08 as U.S. Patent No. 6,955,661), mailed Jul. 11, 2002.
Non-Final Office Action for U.S. Appl. No. 09/411,797 (listed on SB-08 as U.S. Patent No. 6,955,661), mailed Oct. 24, 2003.
Non-Final Office Action for U.S. Appl. No. 09/411,797 (listed on SB-08 as U.S. Patent No. 6,955,661), mailed Mar. 24, 2003.
Non-Final Office Action for U.S. Appl. No. 09/411,797 (listed on SB-08 as U.S. Patent No. 6,955,661), mailed Sep. 24, 2003.
Final Office Action for U.S. Appl. No. 09/411,797 (listed on SB-08 as U.S. Patent No. 6,955,661), mailed Mar. 11, 2004.
Advisory Action for U.S. Appl. No. 09/411,797 (listed on SB-08 as U.S. Patent No. 6,955,661), mailed Jun. 10, 2004.
Notice of Allowance for U.S. Appl. No. 09/411,797 (listed on SB-08 as U.S. Patent No. 6,955,661), mailed Nov. 4, 2004.
Non-Final Office Action for U.S. Appl. No. 11/068,680 (listed on SB-08 as U.S. Patent No. 7,740,793), mailed Oct. 7, 2008.
Non-Final Office Action for U.S. Appl. No. 11/068,680 (listed on SB-08 as U.S. Patent No. 7,740,793), mailed Apr. 2, 2009.
Final Office Action for U.S. Appl. No. 11/068,680 (listed on SB-08 as U.S. Patent No. 7,740,793), mailed Nov. 12, 2009.
Notice of Allowance for U.S. Appl. No. 11/068,680 (listed on SB-08 as U.S. Patent No. 7,740,793), mailed Feb. 25, 2010.
The Oxford English Dictionary, Second Edition, 1989, definition of "plastic".
Clauβ, Wolfram, et al., "No Difference Among Modern Contrast Media's Effect on Neointimal Proliferation and Restenosis After Coronary Stenting in Pigs," *Investigative Radiology*, vol. 38(12):743-749 (2003).
Salu, K.J., et al., "Latrunculin A inhibits smooth muscle cell proliferation I neointimal formation in a porcine coronary stent model," *European Heart Journal*, vol. 4:143 (2002).
Scheller, Bruno, et al., "Addition of Paclitaxel to Contrast Media Prevents Restenosis After Coronary Stent Implantation," *Journal of the American College of Cardiology*, vol. 42(8):1415-1420 (2003).
Scheller, Bruno, et al., "Paclitaxel Balloon Coating, a Novel Method for Prevention and Therapy of Restenosis," *Circulation*, vol. 110:810-814 (2004).
Scheller, B., et al., "Intracoronary paclitaxel added to contrast media inhibits in-stent restenosis of porcine coronary arteries,"*European Heart Journal*, vol. 4:188 (2002).
Scheller, B., et al., "Lack of cardiotoxicity after intracoronary paclitaxel application," *European Heart Journal*, vol. 4:295 (2002).
Scheller, B., et al., "Short-term exposure of vascular smooth muscle cells (VSMC to a contrast medium-paclitaxel formulation inhibits proliferation in vitro," *European Heart Journal*, vol. 4:536 (2002).
Scheller, Bruno, "Paccocath ISR I trial," Euro PCRO5 presentation, 2005.
van der Giessen, Wim, "Glimpse into the future—Part II, Beyond the DES, A Nitric Oxide Eluting System," *Euro PCR*, presentation, 2005.
International Search Report for Application No. PCT/US04/30173, dated Mar. 8, 2006.
International Search Report for Application No. PCT/US04/30541, dated Apr. 17, 2006.
International Search Report for Application No. PCT/US08/061419, dated Sep. 29, 2008.
International Search Report for Application No. PCT/US06/038861, dated Mar. 5, 2007.
Non-final Office Action for U.S. Appl. No. 10/943,075 (listed on SB/08 as US 2005/0113687), mailed Apr. 29, 2008.
Non-final Office Action for U.S. Appl. No. 10/943,075 (listed on SB/08 as US 2005/0113687), mailed Jan. 7, 2009.
Non-final Office Action for U.S. Appl. No. 11/250,768 (listed on SB/08 as US 2006/0112536), mailed Jun. 2, 2008.
Final Office Action for U.S. Appl. No. 11/250,768 (listed on SB/08 as US 8,021,331), mailed Nov. 12, 2008.
Non-final Office Action for U.S. Appl. No. 11/250,768 (listed on SB/08 as US 8,021,331), mailed Jul. 7, 2009.
Final Office Action for U.S. Appl. No. 11/250,768 (listed on SB/08 as US 8,021,331), mailed Dec. 24, 2009.
Non-final Office Action for U.S. Appl. No. 11/250,768 (listed on SB/08 as US 8,021,331), mailed Jul. 7, 2010.
Final Office Action for U.S. Appl. No. 11/250,768 (listed on SB/08 as US 8,021,331), mailed Nov. 9, 2010.
Notice of Allowance for U.S. Appl. No. 11/250,768 (listed on SB/08 as US 8,021,331), mailed Feb. 17, 2011.
Notice of Allowance for U.S. Appl. No. 11/250,768 (listed on SB/08 as US 8,021,331), mailed May 26, 2011.
Non-final Office Action for U.S. Appl. No. 13/102,876 (listed on SB/08 as 8,308,684), mailed Dec. 16, 2011.
Final Office Action for U.S. Appl. No. 13/102,876 (listed on SB/08 as 8,308,684), mailed Apr. 23, 2012.
Notice of Allowance for U.S. Appl. No. 13/102,876 (listed on SB/08 as 8,308,684), mailed Jul. 26, 2012.

* cited by examiner

EXPANDABLE FLUOROPOLYMER DEVICE FOR DELIVERY OF THERAPEUTIC AGENTS AND METHOD OF MAKING

REFERENCE TO RELATED APPLICATIONS

This application is a continuation of U.S. application Ser. No. 11/068,680, filed Feb. 28, 2005, now U.S. Pat. No. 7,740, 793 which is a divisional application of U.S. patent application Ser. No. 09/411,797 (now U.S. Pat. No. 6,955,661), filed Oct. 1, 1999, which claims priority to U.S. Provisional Application Ser. No. 60/117,152, filed Jan. 25, 1999. This application claims the benefit of and priority to the aforementioned applications, which are hereby incorporated herein by reference.

BACKGROUND OF THE INVENTION

Catheter delivered inflatable balloons are utilized in a wide range of surgical procedures to dilate, obstruct, or restore patency to body vessels and organs, as well as to maintain the position of catheter delivered instruments in vivo. Such balloons are typically attached to the distal tip of a small diameter catheter tube to facilitate delivery of the balloon to a treatment site within the body. The balloon is advanced by the catheter through a body vessel while in a deflated condition until the balloon is appropriately positioned proximate the treatment site. The balloon is inflated by infusing a fluid, such as saline, a contrast media, or water, into the balloon through an inflation lumen provided in the catheter. The inflated balloon is deflated after treatment and subsequently removed from the body.

Perforated and porous catheter balloons have been proposed to deliver therapeutic agents, e.g. drugs and other medicinal agents, directly to the treatment site while concomitantly performing their primary function of dilation, obstruction, etc. The localized delivery of therapeutic agents to the treatment site can increase the effectiveness of the therapeutic agent and minimize or even negate the systemic side effects of the agent. Generally, the therapeutic agent is delivered through the wall of the catheter either through openings mechanically formed in the wall or through pores present in the material used to form the balloon. A problem common to such conventional catheter balloons is that the flow-rate and the uniform delivery of fluid, and hence the therapeutic agent, through the walls of the balloon is difficult to control. Successful delivery of the therapeutic agent to the treatment site requires the therapeutic agent to penetrate the body tissue at the treatment site to a depth sufficient for the agent to effect the treatment site without effecting healthy tissue or organs proximate the tissue site. For this reason, the flow rate of and the uniform delivery of the therapeutic agent through the walls of the balloon is important. If the flow rate is too low, the therapeutic agent can fail to properly penetrate the tissue at treatment site. If the flow rate is too high, the therapeutic agent can be delivered to areas of the body outside of the treatment area and, in some cases, elevated flow rates can result in the formation of high velocity fluid jets which can traumatize the tissue adjacent the walls of the balloon.

SUMMARY OF THE INVENTION

The present invention provides a radially expandable fluid delivery device for delivering fluid to a treatment site within the body. The radially expandable fluid delivery device can be used, for example, as a catheter delivered balloon for the treatment of body lumens, organs, and grafts. Fluids, including therapeutic agents, can be delivered through the walls of the fluid delivery device to effect localized treatment of sites within the body. The fluid delivery device of the present invention is constructed of a biocompatible material having a microstructure that can provide a controlled, uniform, low-velocity distribution of fluid through the walls of the fluid delivery device to effectively deliver the fluid to the treatment site without damaging tissue proximate the walls of the device.

In accordance with one aspect of the present invention, the fluid delivery device comprises a member constructed of a biocompatible material. The member is defined by a wall having a thickness extending between an inner and an outer surface. The wall is characterized by a microstructure of nodes interconnected by fibrils. The member is deployable from a first, reduced diameter configuration to a second, increased diameter configuration upon the introduction of a pressurized fluid to the lumen. The pressurized fluid may be introduced at a pressure between about 1 psi to about 250 psi. The member includes at least one microporous portion having a porosity sufficient for the pressurized fluid to permeate through the wall. The spaces between the nodes control the permeation of fluid through the wall of the fluid delivery device. In a preferred embodiment, substantially all of the nodes within the microporous portion are oriented such that spaces between the nodes form generally aligned microchannels extending from the inner surface to the outer surface of the wall.

In accordance with another aspect of the present invention, the nodes within the microporous portion of the member can be oriented substantially parallel to the longitudinal axis of the member. The micro-channels are preferably sized to permit the passage of the pressurized fluid from the inner surface to the outer surface of the wall. The size of the microchannels within the microporous portion can be varied longitudinally and/or circumferentially to provide regions of increased porosity within the microporous portion. The presence of regions of differing porosity allows the volume of fluid delivered through the microporous portion of the member to vary, longitudinally and/or circumferentially, across the microporous portion. This allows the microporous portion to be specifically tailored to the size and shape of the site being treated.

Various biocompatible materials are suitable for the construction of the member. Expanded polytetrafluoroethylene (ePTFE), which is a hydrophobic, biocompatible, inelastic material having a low coefficient of friction, is the preferred material of choice.

In accordance with a further aspect of the present invention, the member can be provided with first and second microporous portions, each having a porosity sufficient for the pressurized fluid to permeate through the wall of the member. The first and second microporous portions can be spaced apart longitudinally and/or circumferentially. An impermeable or semi-permeable portion can be interposed between the first and second microporous portions. Further microporous portions and/or impermeable or semi-permeable portions can also be provided on the member. The microporous portions and the impermeable portions can be arranged in numerous alternative configurations. For example, microporous ring-shaped portions can be spaced along the longitudinal axis of the member. Alternatively, the microporous portions can be generally rectangular in shape and can be spaced apart about the circumference of the member. The provision of multiple microporous portions allows the fluid delivery device of the present invention to treat multiple sites within the body simultaneously.

In accordance with one aspect of the present invention, a method is provided for manufacturing a radially expandable device for delivery of a fluid to a treatment site within the body. The method includes the step of forming a tube of inelastic, fluoropolymer material through an extrusion and expansion process having selected process parameters. The tube has a porosity corresponding to the selected process parameters. A radial expansion force is applied to the tube to expand the tube from an initial diameter to a second diameter. The expansion force is then removed. The resultant tube is radially expandable from a reduced diameter to the second diameter upon application of a radial deployment force from a deployment mechanism within the tube. The deployment mechanism can be, for example, a fluid injected into the tube or a radial expansion element inserted into the tube.

The tube can be constructed through an extrusion and expansion process, including the step of creating a billet by blending a mixture of a fluoropolymer and a lubricant and compressing the mixture. The fluoropolymer is preferably PTFE. The billet can then be extruded to form an extruded article. The lubricant is removed and the extruded article is expanded to form a monolithic tube of inelastic, expanded fluoropolymer material. The stretched tube is then heat set to lock in the microstructure of the tube and maintain the tube in the stretched state.

In accordance with a further aspect of the present invention, at least one of the extrusion and expansion process parameters can be varied to form a microporous portion of the wall having a porosity sufficient for the pressurized fluid to permeate through the wall. For example, the lubricant density, the lubricant viscosity, the lubricant molecular weight, the amount of lubricant and/or the longitudinal stretch ratio can be selectively varied to form the microporous portion of the tube. The process parameters can also be varied to produce increased regions of porosity with the microporous region or to form multiple microporous regions.

The extruded article is preferably bilaterally stretched in two opposing directions along the longitudinal axis of the article. Bilaterally stretching the extruded article yields an article that is substantially uniformly stretched over a major portion of its length and has a microstructure of nodes interconnected by fibrils. Bilateral stretching can further result in the formation of a microstructure in which the nodes are oriented substantially perpendicular to the longitudinal axis of the article such that the spaces between the nodes form microchannels extending from the inner to the outer surface of the wall of the member. The bilateral stretching step can be carried out by displacing the ends of the extruded article either simultaneously or sequentially.

In accordance with another aspect of the present invention, the step of applying a radial expansion force to the tube is carried out by inserting a balloon into the tube and expanding the balloon to apply the radial expansion force to the tube. Preferably, the balloon is constructed from an inelastic material such as, for example, polyethylene terephthalate (PET), nylon, or ePTFE. In a preferred embodiment, the balloon is constructed to be expandable to a predefined size and shape by inflation with a fluid. Radial expansion of the expanded fluoropolymer tube with such an inelastic balloon imparts the predetermined size and shape of the balloon to the expanded fluoropolymer balloon.

In accordance with a further aspect of the present invention, the step of radially expanding the expanded fluoropolymer tube plastically deforms the tube beyond its elastic limit to the second diameter. Plastically deforming the fluoropolymer tube to the second diameter contributes to the expansion device dependably expanding to the second diameter upon application of the radial deployment force.

The step of radially expanding the expanded fluoropolymer tube can also include the steps of positioning the tube within the internal cavity of a mold fixture and radially expanding the balloon within the tube while the tube remains positioned in the internal mold cavity. The internal mold cavity preferably has a size and shape analogous to the predefined size and shape of the balloon. The internal cavity of the mold facilitates concentric radial expansion of the balloon and the fluoropolymer tube.

In accordance with a further aspect of the present invention, the radially expandable fluid delivery of the present invention is particularly suited for treatment of body passages and grafts occluded by disease. The fluid delivery device can be utilized in the manner of a catheter balloon suitable for deployment within a body vessel by a catheter. Exemplary treatment applications of the present application include dilation of stenoic blood vessels in a percutaneous transluminal angioplasty procedure (PCA), removal of thrombi and emboli from obstructed blood vessels, urethra dilation to treat prostatic enlargement due to benign prostate hyperplasia (BPH) or prostatic cancer, and generally restoring patency to body passages such as blood vessels, the urinary tract, the intestinal tract, the kidney ducts, or other body passages. Exemplary therapeutic agents that can be delivered through the fluid delivery device of the present invention include thrombolytics, antibiotics, antisense oligonucleaotides, chemotherapeutics, surfactants, diagnostic agents, steroids, vasodilators, vasoconstrictors, and embolic agents.

BRIEF DESCRIPTION OF THE DRAWINGS

These and other features and advantages of the present invention will be more fully understood by reference to the following detailed description in conjunction with the attached drawings in which like reference numerals refer to like elements through the different views. The drawings illustrate principles of the invention and, although not to scale, show relative dimensions.

DETAILED DESCRIPTION OF THE PREFERRED EMBODIMENTS

Figure 1:
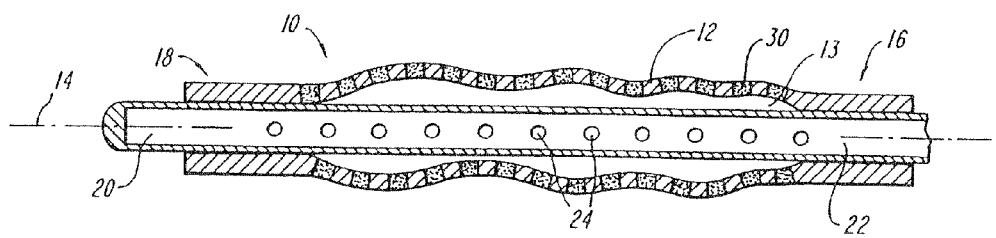
FIG. 1 is a side elevational view in cross-section of a radially expandable fluid delivery device according to the teachings of the present invention, illustrating the device in a first, reduced diameter configuration.
Figure 2:
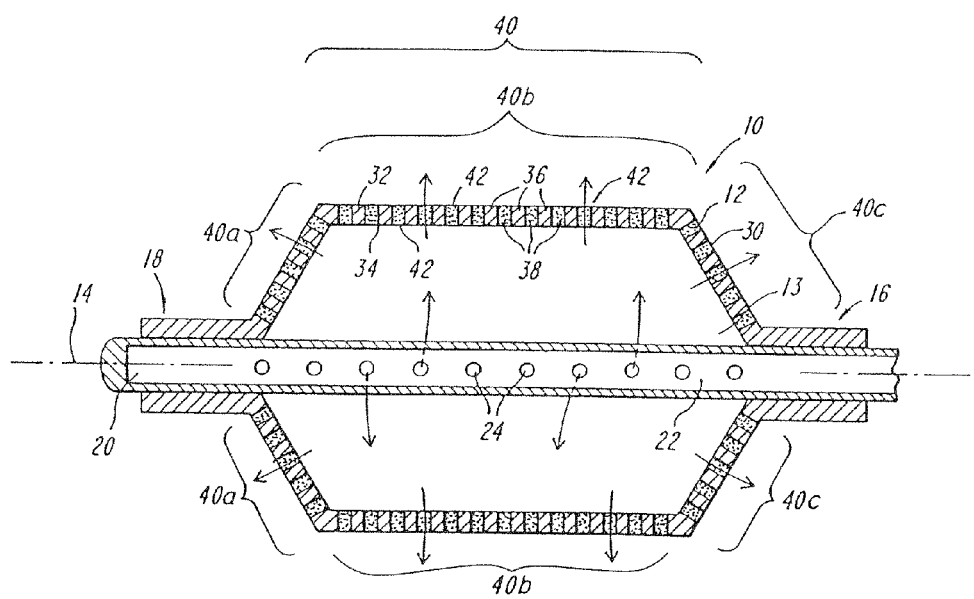
FIG. 2 is a side elevational view in cross-section of the radially expandable fluid delivery device of FIG. 1, illustrating the device in a second, increased diameter configuration.

A radially expandable fluid delivery device 10 having an extensible member 12 constructed of a biocompatible fluoropolymer material is illustrated in FIGS. 1 and 2. The radially expandable fluid delivery device 10 of the present invention is suitable for a wide range of treatment applications. Such applications include use of the fluid delivery device 10 as a catheter balloon for treatment of body passages and grafts such as blood vessels, the urinary tract, the intestinal tract, kidney ducts, natural and synthetic grafts, etc. Specific examples include as a device for the removal of obstructions such as emboli and thrombi from blood vessels, as a dilation device to restore patency to an occluded body passage, as an occlusion device to selectively obstruct a body passage, and as a centering mechanism for transluminal instruments and catheters. In each of these applications, the fluid delivery device 10 can simultaneously deliver a fluid, such as a therapeutic agent, to the body vessel, or the tissue or organs surrounding the body vessel, to effect local treatment with the agent.

The extensible member 12 of the radially expandable fluid delivery device 10 is deployable upon application of an expansion force from a first, reduced diameter configuration, illustrated in FIG. 1, to a second, increased diameter configuration, illustrated in FIG. 2. The extensible member 12 of the fluid delivery device 10 of the present invention preferably features a monolithic construction, i.e., the extensible member 12 is a singular, unitary article of generally homogeneous material. The extensible member 12 is manufactured in accordance with the methods of manufacturing of the present invention, an extrusion and expansion process described in detail below, to yield an extensible member 12 characterized by a seamless construction of inelastic, expanded fluoropolymer having a predefined size and shape in the second, increased diameter configuration. The extensible member 12 can be dependably and predictably expanded to the predefined, fixed maximum diameter and to the predefined shape independent of the expansion force used to expand the device.

Referring specifically to FIG. 2, the extensible member 12 of the fluid delivery device 10 of the present invention is generally tubular in shape when expanded, although other cross sections, such as rectangular, oval, elliptical, or polygonal, can be utilized. The cross-section of the extensible member 12 is continuous and uniform along the length of the extensible member. However, in alternative embodiments, the cross-section can vary in size and/or shape along the length of the extensible member. FIG. 1 illustrates the extensible member 12 relaxed in the first, reduced diameter configuration. The extensible member 12 has a central lumen 13 extending along a longitudinal axis 14 between a first end 16 and second end 18.

A deployment mechanism in the form of an elongated hollow tube 20 is shown positioned within the central lumen 13 to provide a radial deployment or expansion force to the extensible member 12. The tube 20 can be, for example, a catheter constructed from PEBAX tubing available from Elf Atochem of France. The tube 20 is selected to have an outer diameter approximately equal to the diameter of the central lumen 13 of the extensible member 12 in the reduced diameter configuration. The radial deployment force effects radial expansion of the extensible member 12 from the first configuration to the second increased diameter configuration illustrated in FIG. 2. The first end 16 and the second end 18 are connected in sealing relationship to the outer surface of the hollow tube 20. The first and second ends 16 and 18 can be thermally bonded, bonded by means of an adhesive, or attached by other means suitable for inhibiting fluid leakage from the first and second ends 16 and 18 between the walls of the extensible member 12 and the tube 20.

The hollow tube 20 includes an internal, longitudinal extending lumen 22 and a number of side-holes 24 that provide for fluid communication between the exterior of the tube 20 and the lumen 22. The tube 20 can be coupled to a fluid source (not shown) to selectively provide fluid, such as water, a contrast medium, of saline, to the lumen 13 of the extensible member 12 through the lumen 22 and side-holes 24. The pressure from the fluid provides a radial expansion force on the extensible member 12 to radial expand the extensible member 12 to the second, increased diameter configuration. Because the extensible member 12 is constructed from an inelastic material, uncoupling the tube 20 from the fluid source or otherwise substantially reducing the fluid pressure within the lumen 13 of the extensible member 12, does not generally result in the extensible member 12 returning to the first, reduced diameter configuration. However, the extensible member 12 will collapse under its own weight to a reduced diameter. Application of negative pressure, from, for example, a vacuum source, can be used to completely deflate the extensible member 12 to the initial reduced diameter configuration.

One skilled in the art will appreciate that the expansion device 10 of the present invention is not limited to use with deployment mechanisms employing a fluid deployment force, such as hollow tube 20. Other known deployment mechanisms can be used to radially deploy the expansion device 10 including, for example, mechanical operated expansion elements, such as mechanically activated members or expansion elements constructed from temperature activated materials such as nitinol.

The extensible member 12 is defined by a wall 30 of biocompatible fluoropolymer material having a thickness extending between an outer surface 32 and an inner surface 34 of the extensible member 12. The inner surface 34 defines the lumen 13 of the extensible body 12. The wall 30 of biocompatible fluoropolymer material is characterized by a microstructure of nodes interconnected by fibrils. FIGS. 1 and 2 provide schematic representations of the microstructure of the extensible member 12. For purposes of description, the microstructure of the extensible member has been exaggerated. Accordingly, while the dimensions of the microstructure are enlarged, the general character of the illustrated microstructure is representative of the microstructure of the extensible member 12.

The extensible member 12 includes at least one microporous portion 40 having a porosity sufficient for the flow of fluid from the lumen 13 through the wall 30, i.e. from inner surface 34 to outer surface 32. The microstructure of the wall 30 within the microporous portion 40 is characterized by a plurality of nodes 36 interconnected by fibrils 38. Preferably, all or substantially all of the nodes 36 within the microporous portion 40 are oriented perpendicular to the inner surface 34 and the outer surface 32 of the extensible member 12 as well as parallel to each other. This preferred orientation of the nodes 36 provides internodal spaces that form pores or micro-channels 42 that extend between the inner surface 34 and the outer surface 32 of the extensible member 12. The micro-channels 42 are sized to permit the flow of fluid between the nodes 36 through the wall 30.

The size of the micro-channels or pores 42 can be selected through the manufacturing process of the present invention, described in detail below. Preferably, the internodal distance of microstructure of the wall within the microporous region, and hence the width of the micro-channels, is approximately 1 µm to approximately 150 µm. Internodal distances of this magnitude can yield flow rates of approximately 0.01 ml/min to approximately 100 ml/min of fluid through the wall 30 of the extensible member 12.

In a preferred embodiment, the size of the micro-channels or pores 42 within the microporous portion 40 is uniform throughout the microporous portion. In this manner, the flow-rate of fluid through the wall of the microporous portion 40 is also generally uniform. In some applications, however, it may be desirable to have an area of increased or decreased porosity within the microporous portion such that the flow-rate can be tailored to the particular geometry of the site being treated. For example, if a particular region at the treatment site requires increased concentrations of the therapeutic agent, the flow rate at the corresponding section of the microporous portion can be increased to thereby increase the volume of therapeutic agent be delivered to the particular region. Additionally, it is often desirable to reduce the volume of therapeutic agent delivered to the periphery of the treatment site to minimize damage to healthy tissue adjacent the site. The pore size within the microporous region thus can be varied axially or circumferentially, or both, to form such areas of increased or decreased porosity.

The terms "axial" and "axially" as used herein refers to a direction generally parallel to the longitudinal axis of the extensible member 12. The terms "circumferential" and "circumferentially" as used herein refers to a direction generally parallel to the circumference of the extensible member 12. The explanation of these terms is not, however, to be construed to limit the extensible member 12 to a circular cross-section. As discussed above, the cross-section can be any of a number shapes. In the case of non-circular cross-sections, the terms "circumferential" and "circumferentially" as used herein to generally refer to a direction parallel to the perimeter of the extensible member.

The axial length, as well as the axial position, of the microporous portion 40 of the extensible member 12 can be varied to accommodate specific treatment applications. As illustrated in FIG. 2, for example, the microporous portion 40 can extend along the entire inflatable length of the extensible member 12. In particular, the microporous portion 40 includes a section 40*b* that is oriented parallel to the longitudinal axis 14 of the extensible member 12 as well as two spaced apart tapered sections 40*b* and 40*c*. In the embodiment illustrated in FIG. 2, thus, the microporous portions 40*a*, 40*b*, and 40*c* extend along the entire length of the extensible member 12, absent the first and second ends 16 and 18, which are sealed to the hollow tube 20.

Figure 3:
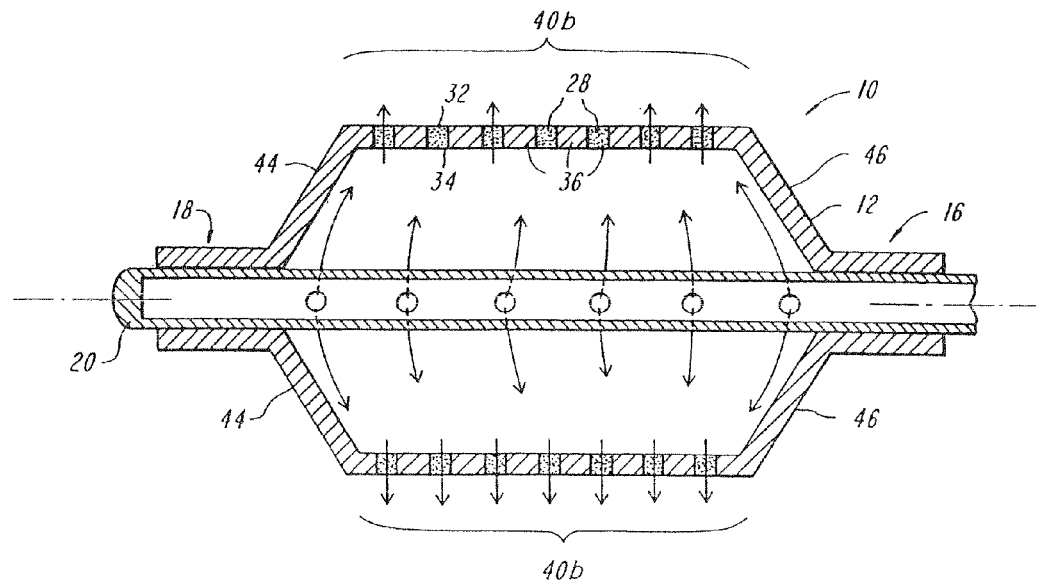
FIG. 3 is a side elevational view of an alternative embodiment of the radially expandable fluid delivery device of the present invention, illustrating the device in the second, increased diameter configuration.

The microporous portion 40 need not extend the entire inflatable length of the extensible member 12 but instead can include only sections of the length of the extensible member 12. For example, as illustrated in FIG. 3, the microporous portion can include only section 40*b*, the section oriented parallel to the longitudinal axis 14 of the extensible member 12. Tapered section 44 and 46 adjacent the microporous portion 40*b* can be substantially impermeable to the fluid within the extensible member 12. The tapered sections 44 and 46 can formed with the same microstructure as the microporous portions 40*b*, i.e. nodes of the same size and orientation, and can be sealed with a coating provided on the inner surface 34 or the outer surface 32 to inhibit fluid flow through the sections 44 and 46. Alternatively, the microstructure of the tapered sections 44 and 46 can have an impermeable, non-porous structure. For example, the nodes forming the microstructure of the tapered sections 44 and 46 can be spaced apart or oriented to inhibit or prevent fluid from passing therethrough.

Figure 4:
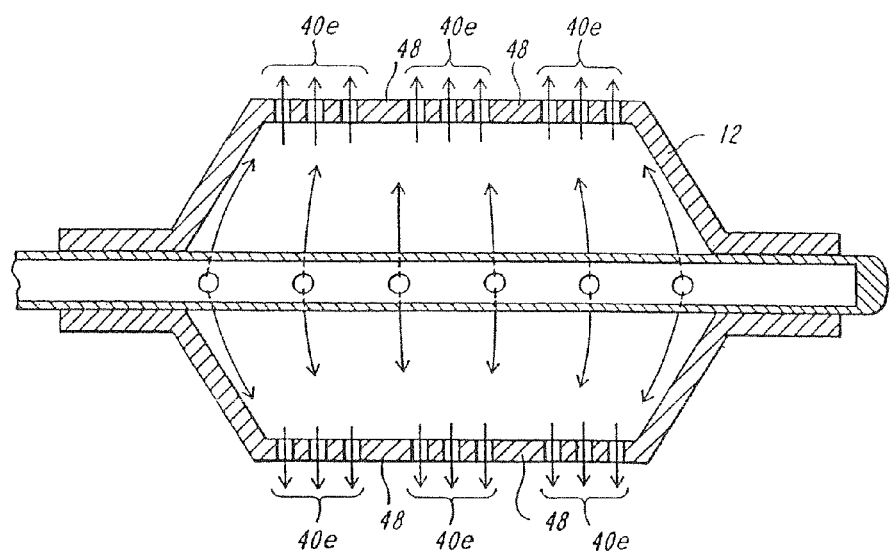
FIG. 4 is a side elevational view of an alternative embodiment of a radially expandable fluid delivery device of the present invention having multiple axially-spaced microporous portions, illustrating the device in the second, increased diameter configuration.

Moreover, two or more microporous portions of similar or different axial lengths can be provided on the extensible member 12. For example, the extensible member 12 can be provided with three axially spaced microporous portions 40*e*, as shown in FIG. 4. Each of the microporous portions 40*e* is bordered axially by an impermeable portion 48. The microporous portions 40*e* provide porous, fluid permeable annular zones that are spaced lengthwise along the extensible member 12. The microporous portions 40*e* can be equally spaced and of similar size, as illustrated in FIG. 4, or, in the alternative, can be distinctly sized and spaced. One skilled in the art will appreciate that the number of independent microporous portions is not limited to three as shown in FIG. 4, but can include two or more zones as dictated by the length of the extensible member 12 and the desired size of the microporous portions.

Figure 5:
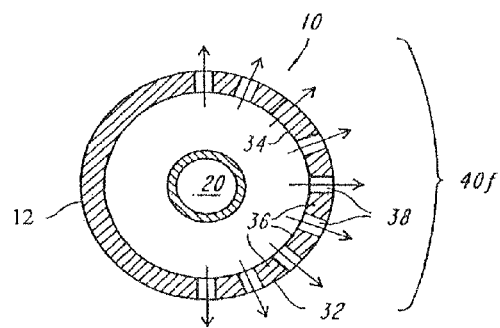
FIG. 5 is a cross-sectional view of an alternative embodiment of a radially expandable fluid delivery device of the present invention having an arcuate-shaped microporous portion, illustrating the device in the second, increased diameter configuration.
Figure 6:
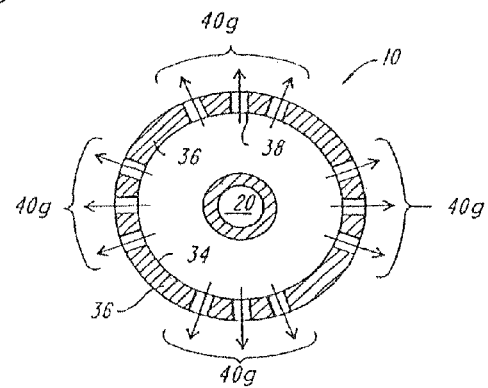
FIG. 6 is a cross-sectional view of an alternative embodiment of a radially expandable fluid delivery device of the present invention having multiple circumferentially-spaced microporous portions, illustrating the device in the second, increased diameter configuration.

Referring to FIGS. 5 and 6, the size and position of the microporous portion can be varied circumferentially as well as axially. For example, the microporous section need not extend about the entire circumference of the extensible member 12. FIG. 5 illustrates an alternative embodiment in which the microporous portion 40f generally extends about one-half of the circumference of the extensible member to form an arc-shaped section that is permeable to fluid within the extensible member 12. An impermeable arc-shaped section 50 is positioned adjacent the arc-shaped microporous portion 40f. Additionally, two or more microporous portions can be spaced circumferentially about the extensible member 12. FIG. 6 shows an alternative embodiment including four equally spaced arcuate microporous portions 40g. Arc-shaped impermeable portions 52 are spaced between the microporous portions 40g. As in the case of the embodiments described above, the microporous portions 40g can be equally spaced and of similar size, as illustrated in FIG. 6, or, in the alternative, can distinctly sized and spaced. Further, the number of microporous portions described is exemplary only; the number of microporous portions is limited only by the circumference of the extensible member 12 and the desired size of the microporous portions.

The impermeable sections of each of the embodiments described above can be constructed of the same microstructure as the microporous portions adjacent thereto, i.e. nodes having the same size and orientation. The impermeable sections can be made impermeable by sealing the sections with a coating provided on either the inner surface 34 or the outer surface 32, or both, to inhibit or prevent fluid flow through the sections. Alternatively, the microstructure of the impermeable sections can be constructed to have an inherently impermeable, non-porous structure. For example, the nodes forming the microstructure of the impermeable sections can be spaced apart or oriented to inhibit or prevent fluid from passing therethrough.

Various fluoropolymer materials are suitable for use in the present invention. Suitable fluoropolymer materials include, for example, polytetrafluoroethylene (PTFE) or copolymers of tetrafluoroethylene with other monomers may be used. Such monomers include ethylene, chlorotrifluoroethylene, perfluoroalkoxytetrafluoroethylene, or fluorinated propylenes such as hexafluoropropylene. ePTFE is the preferred material of choice. Accordingly, while the fluid delivery device 10 can be manufactured from various fluoropolymer materials, and the manufacturing methods of the present invention can utilize various fluoropolymer materials, the description set forth herein refers specifically to ePTFE.

A method of manufacturing a fluid delivery device in accordance with the present invention will be described in connection with the flow chart shown in FIG. 7. The fluid delivery device 10 of the present invention is produced from a tube constructed of expanded fluoropolymer material, which is preferably produced through an extrusion and a longitudinal expansion process. The preferred fluoropolymer material is expanded PTFE (ePTFE), which is a hydrophobic, biocompatible, inelastic material having a low coefficient of friction, although, as discussed above, other inelastic, biocompatible fluoropolymer materials may be used.

To produce the ePTFE tube, a billet comprising a PTFE resin mixed with an organic lubricant is utilized. Various organic lubricants are suitable such as naphtha, ISOPAR-G and ISOPAR-H available from Exxon Corporation. The blended resin is compressed at low pressure to yield a tubular billet of PTFE resin and lubricant, step 210 of FIG. 7. The tubular billet is then extruded through an extruder, for example a ram extruder, to reduce the cross section of the billet and to yield a tubular extrudate, ram extruder, to reduce the cross section of the billet and to yield a tubular extrudate, step 212. The organic lubricant can be removed from the extrudate by drying the extrudate in a heated oven, step 214.

Once the tubular extrudate is produced, the extrudate is expanded by longitudinal stretching, step 216. Preferably, the extrudate is bilaterally stretched. Bilateral stretching is accomplished by displacing both ends of the extrudate, sequentially or simultaneously, away from the center of the extrudate. Bilateral stretching provides a material that is homogeneously stretched over the majority of its length and yields a uniform porosity over the length of the material. After the extrudate has been stretched, it is heat set to lock in the microstructure of the material, step 218 of FIG. 7, and to complete the process of the forming the tube 110 of ePTFE.

Figure 8:
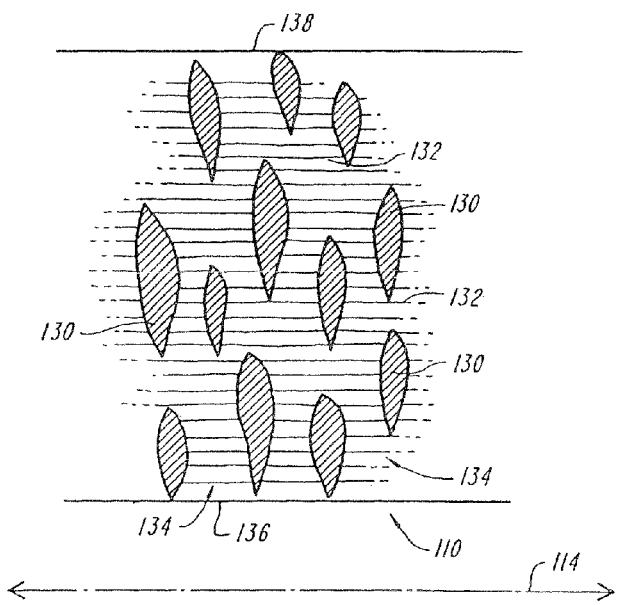
FIG. 8 is a schematic representation of the microstructure of an expanded fluoropolymer tube used during the manufacturing process of the present invention to yield the fluid delivery device of FIG. 1.

FIG. 8 is a schematic representation of the ePTFE tube 110 as formed by the extrusion and expansion process described above. For purposes of description, the microstructure of the tube 110 has been exaggerated. Accordingly, while the dimensions of the microstructure are enlarged, the general character of the illustrated microstructure is representative of the microstructure prevailing within the tube 110.

The microstructure of the ePTFE tube 110 is characterized by nodes 130 interconnected by fibrils 132. The nodes 130 are generally aligned with one another and are generally oriented perpendicular to the longitudinal axis 114 of the tube 110. Substantially all of the nodes 130 extend along a transverse axis 114 from an inner surface 136 to an outer surface 138 of the tube 110. This microstructure of nodes 130 interconnected by fibrils132 provides a microporous structure having microfibrillar spaces which define generally aligned through-pores or channels 134 extending entirely from the inner wall 136 and the outer wall 138 of the tube 110. The through-pores 134 are perpendicularly oriented (relative to the longitudinal axis114), internodal spaces that traverse from the inner wall 136 to the outer wall 138. The size and geometry of the through-passages can be altered through the extrusion and expansion process, to yield a microstructure that is impermeable, semi-impermeable, or permeable.

Although it is preferable for the micro-channels of the ePTFE tube 110, and the resultant fluid delivery device 10, to be oriented generally perpendicular to the longitudinal axis of the tube ePTFE 110 or fluid delivery device 10, other orientations of the micro-channels can be utilized. For example, by twisting or rotating the ePTFE tube during the extrusion and/or stretching process, the micro-channels can be oriented at an angle to an axis perpendicular to the longitudinal axis of the tube.

In a preferred embodiment, the ePTFE tube 110, and the resultant fluid delivery device 10, has a fine nodal structure that is uniform throughout the cross section and length of the ePTFE tube. The preferred uniform fine nodal structure provides the fluid delivery device 10 with improved expansion characteristics as the expandable device dependably and predictably expands to the second diameter. The preferred fine nodal structure is characterized by nodes having a size and mass less than the nodes found in conventional ePTFE grafts, preferably in the range of 25 µm to 30 µm. Additionally, the spacing between the nodes, referred to as the internodal distance, and the spacing between the fibers, referred to as the interfibril distance, is also preferably less than found in conventional ePTFE grafts, preferably in the range of 1 µm to 5

µm. Moreover, the internodal distance and the interfibril distance in the preferred embodiment is preferably uniform throughout the length and the cross section of the ePTFE tube. The preferred uniform nodal structure can be created by forming the billet with a uniform lubricant level throughout its cross section and length. Stretching the tubular extrudate at higher stretch rates, for example at rates greater than 1 in/s, yields the preferred fine nodal structure. Preferably, the extrudate is stretched at a rate of approximately 10 in/s or greater.

Figure 7:
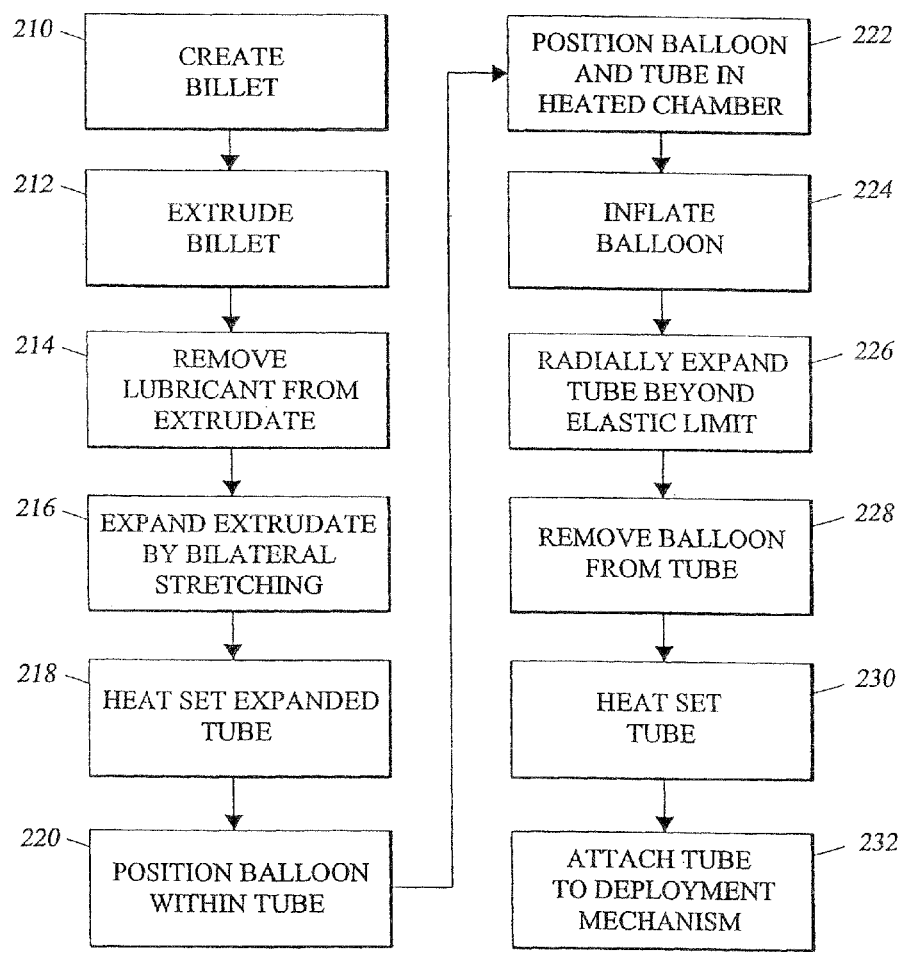
FIG. 7 is a flow chart illustrating the steps of manufacturing a fluid delivery device according to the teachings of the present invention.
Figure 9A:
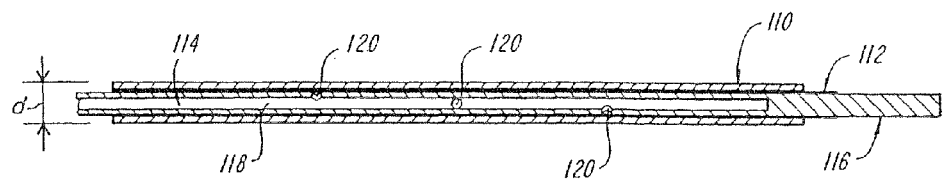
FIG. 9A is a side elevational view in cross-section of an inelastic balloon positioned within an expanded fluoropolymer tube, illustrating the inelastic balloon in a deflated condition in accordance with a method of manufacturing a fluid delivery device according to the teachings of the present invention.

Continuing to describe the manufacturing method of the present invention and referring to FIGS. 7 and 9A, the ePTFE tube 110, having an initial diameter d, is pulled over a balloon 112 to position the balloon 112 within the lumen 114 of the tube 110, step 220 of FIG. 7. The balloon 112 is preferably constructed of an inelastic material such as, for example, PET, nylon, or PTFE, such that the balloon 112, when inflated, attains a predetermined size and shape. The balloon 112 can be bonded or otherwise coupled to a rigid catheter or hypotube 116 to facilitate placement and removal of the ePTFE tube as described below. The catheter 116 has a central inflation lumen 118 and a plurality of side-holes 120 to provide for the delivery of an inflation fluid to inflate the balloon 112. Prior to placement of the ePTFE tube 110 over the balloon 112, a small amount of negative pressure (vacuum) can be applied to the balloon 112 to reduce the balloon to a minimum deflated profile.

Figure 10:
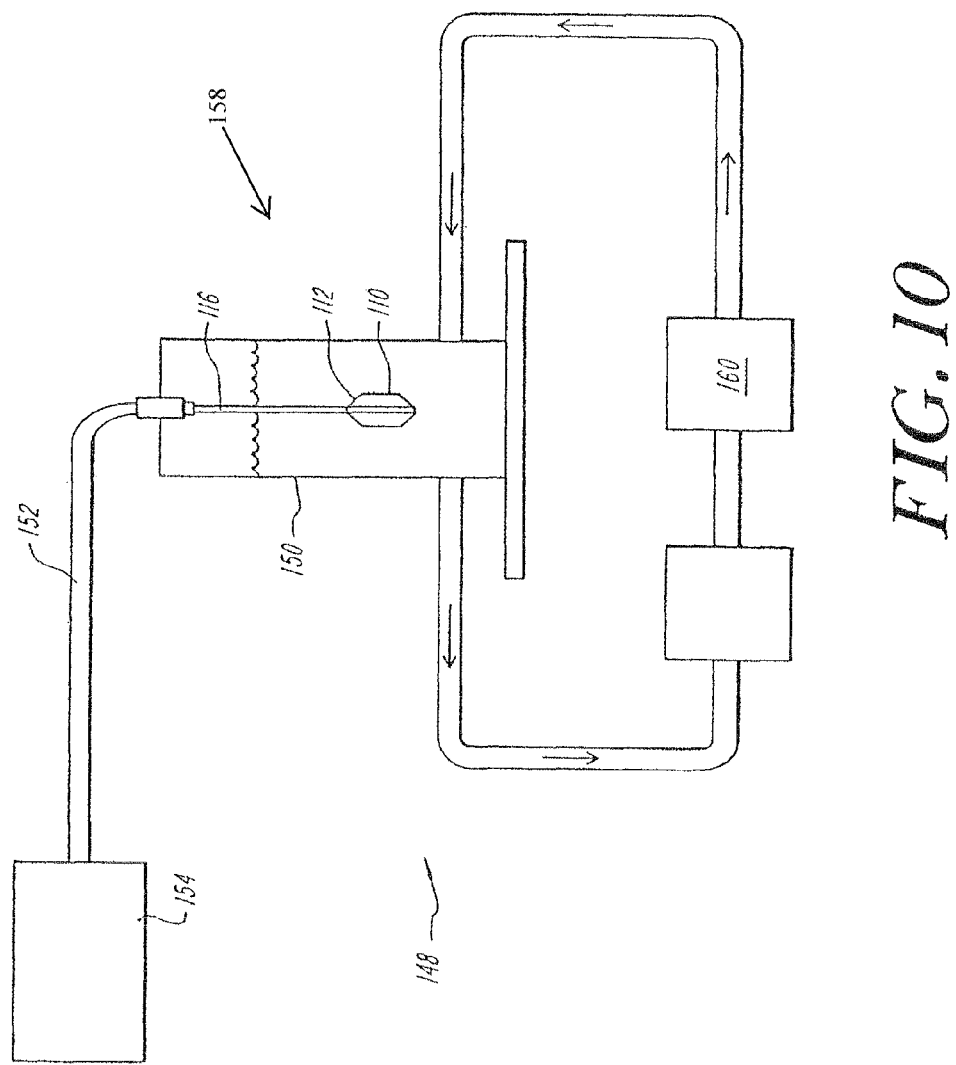
FIG. 10 is a schematic of a system for inflating an inelastic balloon with an expanded fluoropolymer tube in accordance with a method of manufacturing a fluid delivery device according to the teachings of the present invention.

Referring to FIG. 10, a system 148 for inflating the balloon 112 within the ePTFE tube is illustrated. The balloon 112 and the ePTFE tube 110 are positioned within water heated chamber 150, step 222 of FIG. 6. The catheter 116 is connected by plastic tubing 152 to a pump 154, such as an ISCO syringe pump, for inflation of the balloon 112 with a fluid. Heated water from a circulating temperature bath 158 is pumped through the chamber 150 by a pump 160 to maintain the water within the chamber 150 at a desired temperature. The water within the chamber 150 is heated to a temperature between approximately 35° C. and approximately 60° C. The preferred temperature of the water within the chamber 150 is 50° C. The constant, elevated temperature provided by the circulating water can contribute to uniform expansion, both circumferentially and longitudinally, of the ePTFE balloon, as well as uniform wall thickness.

Figure 9B:
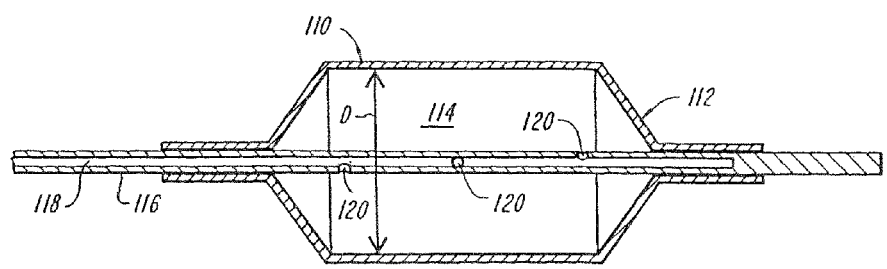
FIG. 9B is a side elevational view in cross-section of the inelastic balloon and the expanded fluoropolymer tube of FIG. 9A, illustrating the inelastic balloon in an inflated condition in accordance with a method of manufacturing a fluid delivery device according to the teachings of the present invention.

Referring to FIGS. 9B and 10, the balloon 112 can be inflated by introduction of pressurized fluid from the pump 154 to the lumen 114 of the ePTFE tube 110. For example, the pressurized fluid may be introduced at a pressure between about 1 psi to about 250 psi. The overlying ePTFE tube 110 expands with the inelastic balloon 122 until both the balloon 112 and the ePTFE tube 110 obtain the predetermined size and shape of the inflated balloon 112, step 224 of FIG. 7. The inflated balloon 112 thus imparts its predetermined size and shape to the ePTFE tube 110. This radially expansion process is referred to as "blow-molding". The PTFE tube 110 shown in FIG. 9B is radially expanded from the initial diameter d (FIG. 9A) to an increased diameter D.

It is preferable for the ePTFE tube 110 to be plastically deformed by the radial expansion of the inelastic balloon 112, step 226 of FIG. 7. The terms "plastic deformation" and "plastically deform," as used herein, is intended to include the radial expansion of the ePTFE tube 110 beyond the elastic limit of the ePTFE material such that the ePTFE material is permanently deformed. Once plastically deformed, the ePTFE material forming the tube 110 becomes substantially inelastic, i.e., the ePTFE tube generally will not, on its own, return to its pre-expansion size and shape.

Figure 9C:
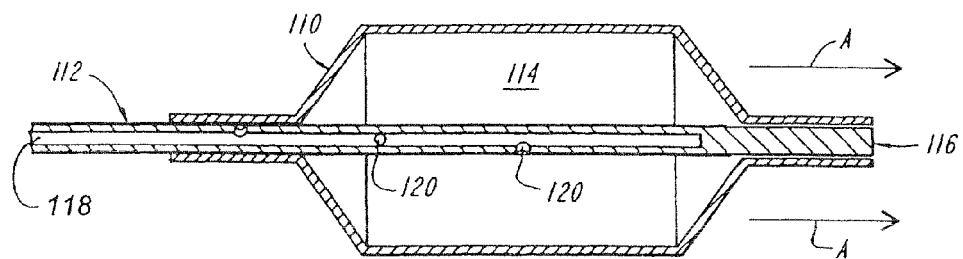
FIG. 9C is a side elevational view in cross-section of the inelastic balloon and the expanded fluoropolymer tube of FIG. 9A, illustrating the removal of the deflated inelastic balloon from the expanded fluoropolymer tube in accordance with a method of manufacturing a fluid delivery device according to the teachings of the present invention.

The ePTFE tube 110 can be removed from the balloon 112 by removing the inflation fluid from the balloon 112 using the pump 154 and sliding the ePTFE tube 110 relative to balloon 112 and catheter 116, i.e. in the direction of arrows A in FIG. 9C, step 228 of FIG. 7. The tube 110 can be heat set at a temperature above the sinter point of the material forming the tube, 360° C. for ePTFE, to lock in the structure of the tube 110, step 230 of FIG. 7. The pump 150 can be used to provide a slight vacuum within the balloon 112 to facilitate removal of the ePTFE tube 110.

The ePTFE tube 110 can be attached to a deployment mechanism such as hollow tube 20 described above, step 232 of FIG. 7. A suitable adhesive can be used to secure the ePTFE tube to the deployment mechanism.

Figure 11:
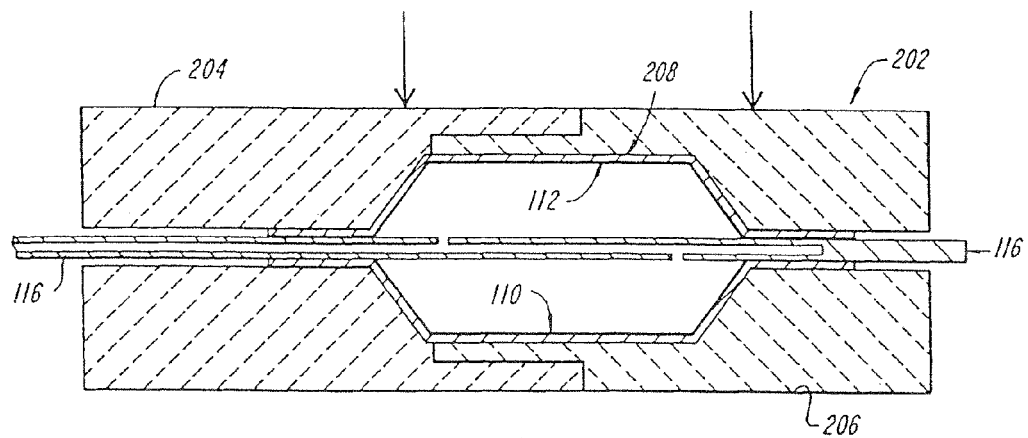
FIG. 11 is a side elevational view of an inelastic balloon and an expanded fluoropolymer tube positioned within the internal cavity of a mold fixture, illustrating the inelastic balloon in an inflated condition in accordance with a method of manufacturing a fluid delivery device according to the teachings of the present invention.

Referring to FIG. 11, an alternative method of manufacturing a radially expandable device employing a mold 202 is illustrated. The mold 202 includes two interconnected sections 204 and 206 forming an internal mold cavity 208 for receiving the ePTFE tube 110 with the balloon 112 positioned therein. The mold 202 is preferably constructed of a rigid, unyielding material such as a metal or metal alloy. Suitable metals or metal alloys include brass and steel alloys. The internal mold cavity 208 preferably has a size and shape analogous to that of the inflated balloon 112 to ensure that the inflated balloon 112, and the overlying ePTFE tube 110 concentrically expand.

Figure 13:
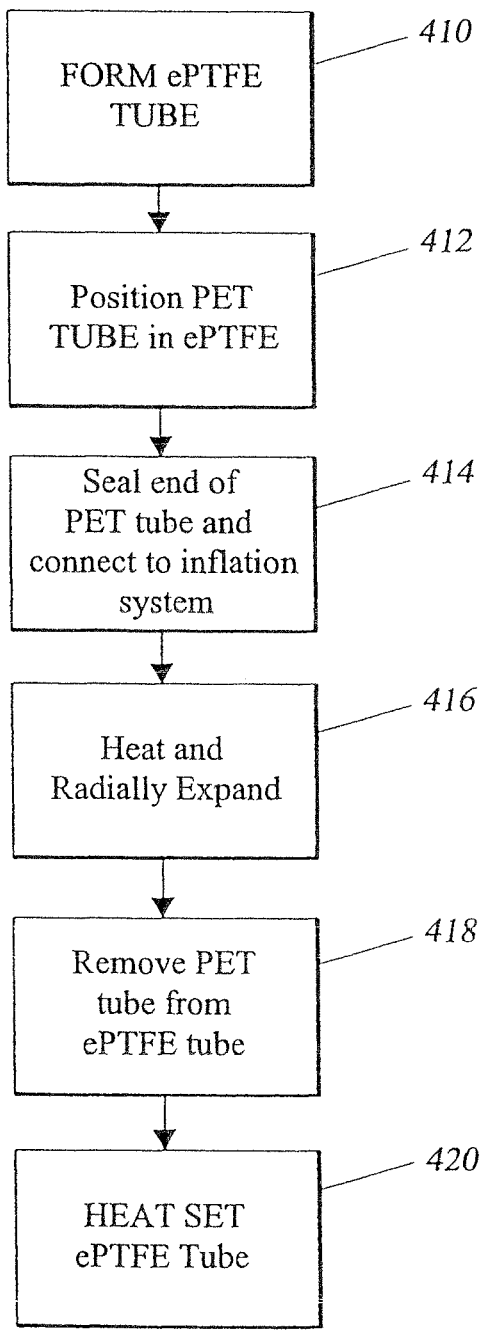
FIG. 13 is a flow chart illustrating the steps of an alternative method of manufacturing a fluid delivery device according to the teachings of the present invention.

Referring to the flow chart illustrated in FIG. 13, a further alternative method of manufacturing a fluid delivery device according to the teachings of the present invention will be described. A tube constructed of ePTFE is formed in accordance with the methods described above, step 410. A tube formed of an extruded inelastic material such as PET is used in place of balloon 112 to radially expand the ePTFE tube. The extruded tube is positioned within the ePTFE tube 110, step 412. The extruded tube is then sealed at one end and attached to an inflation system at the other end, step 414. The extruded tube can then be inflated by an inflation medium to radially expand the ePTFE tube, step 416. The extruded tube and ePTFE tube are preferably heated to the glass transition temperature of the extruded tube, approximately 80° C.-100° C. for PET, as the extruded tube is inflated within the ePTFE tube. It is preferable to limit the temperature of the extruded tube to a temperature less than or equal to the glass transition temperature of the material forming the extruded tube to facilitate removal of the extruded tube from the ePTFE tube. Heating the extruded to a temperature above the glass transition temperature will cause the extruded tube to heat set in an expanded configuration, which makes removing the extruded tube from the ePTFE tube difficult.

After the extruded tube and ePTFE tube are expanded to desired size and shape, the extruded tube is deflated and removed from the ePTFE tube, step 418. The ePTFE tube is then heat set to lock in the structure of the ePTFE tube, step 420.

A mold, such as mold 202, can be employed during radial expansion of the ePTFE tube using the PET tube. The mold is preferably heated within the hot water chamber of an inflation system, such as inflation system 148 illustrated in FIG. 10, or by other means such as a hot oil bath or through a steam, hot air, electric, radio frequency or infra red heat source. The mold can be constructed of a material having good head transfer characteristics, such as metal or metal alloy, for example brass. The mold includes a mold cavity having a size and shape analogous to the desired size and shape of the fluid delivery device 10 in the second diameter configuration.

The resultant radially expanded ePTFE tube 110, produced in accordance with the above described methods, provides a radially expandable fluid delivery device, such as the fluid delivery device 10 illustrated in FIGS. 1 and 2 and described above, that is radially expandable from a relaxed, collapsed diameter to the second, increased diameter D upon application of a radial deployment force from a deployment mechanism within the tube 110. Moreover, the microstructure of the radially expanded ePTFE tube 110 can be manufactured through the process of the present invention to have a porosity sufficient to permit fluid to flow therethrough. In particular, the microstructure of the resultant fluid delivery device is analogous to the microstructure of the ePTFE tube 110, i.e. nodes interconnected by fibrils, the space between the nodes defining micro-channels through the wall of the device.

One feature of the manufacturing processes of the present invention is that the microporous structure of the ePTFE tube 110 forming the fluid delivery device 10 can be manipulated by varying the extrusion and expansion process parameters to produce different porosity characteristics. For example the longitudinal stretch ratio of the ePTFE tube 110, i.e., the ratio of final stretched length of the tube to the initial length, and the diametric stretch ratio of the ePTFE tube 110, i.e., the ratio of the final diameter, after longitudinal stretching, and the initial diameter, and the stretch rate can be varied to yield fluid recovery devices having different porosity. Applicants determined that larger longitudinal stretch ratios, in the order of 2:1 to 3:1, can result in a ePTFE tube having a microstructure characterized by increased internodal distances and interstitial space, i.e., the micro-channels within the microstructure of the ePTFE tube are increase in sized. Suitable longitudinal stretch ratios can be from 1.1:1 to 10:1.

Fluid delivery devices formed from ePTFE tubes having larger stretch ratios require minimal fluid pressure within the device to achieve the desired flow rate of fluid through the walls of the device. Such fluid delivery devices will consequently provide little radially-outward dilation force, which can be advantageous for some applications such as delivering therapuetic or diagnostic agents to healthy tissue. Conversely, ePTFE tubes having smaller stretch ratios result in fluid delivery devices that are less porous, as the internodal distances are reduced, and, thus, generally require increased fluid pressure to deliver the fluid. Such fluid delivery devices consequently provide increased radially outward dilation force, which can be advantageous for treatment applications such as reducing arterial lesions with pressure. Accordingly, the porosity of the ePTFE tube, and hence the porosity of the resultant fluid delivery device, is dependent on the stretch ratios of the expansion process. By manipulating the stretch ratios of the ePTFE tube, i.e. increasing or decreasing the stretch ratios, the porosity of the fluid delivery device can be tailored to the specific treatment application.

The porosity of the ePTFE tube, and the subsequent fluid delivery device, can also depend on the density, the viscosity, the molecular weight, and the amount of lubricant used to form the billet used in the extrusion and expansion process. Increasing the amount by weight of lubricant or increasing the density or molecular weight of the lubricant, results in an extrudate having increased internodal distances and interstitial spaces prior to the step of expansion. Once stretched, the resultant ePTFE tube will reflect the increased porosity.

The process described above can be used to produce fluid delivery devices having a uniform porosity though out the length of the device. To produce discrete microporous portions within the fluid delivery devices a number of different processes can be employed. For example, a coating can be applied at select locations to the inner and/or outer surfaces of the fluid delivery device to produce impermeable sections within the device. The coating preferable seals the micro-channels within the microstructure of the device to inhibit or prevent fluid from passing therethrough.

Alternatively, the porosity of the ePTFE tube can be selectively reduced subsequent to the step of expansion by applying heat to the select sections of the tube to return the sections to the pre-stretched porosity. The selectively heated sections will thus yield sections of reduced porosity. By controlling the amount of heat applied, the sections of reduced porosity can be made semi-permeable or impermeable to fluid.

In addition to selecting and varying the porosity of the fluid recovery device through the manufacturing process of the present invention, the parameters of the manufacturing process can be varied to produce an ePTFE tube having distinct expansion characteristics. The size and shape of the fluid recovery device of the present invention can also be varied. These processes are described in detail in Applicants' U.S. Pat. No. 6,395,208, which is incorporated herein by reference.

Figure 12:
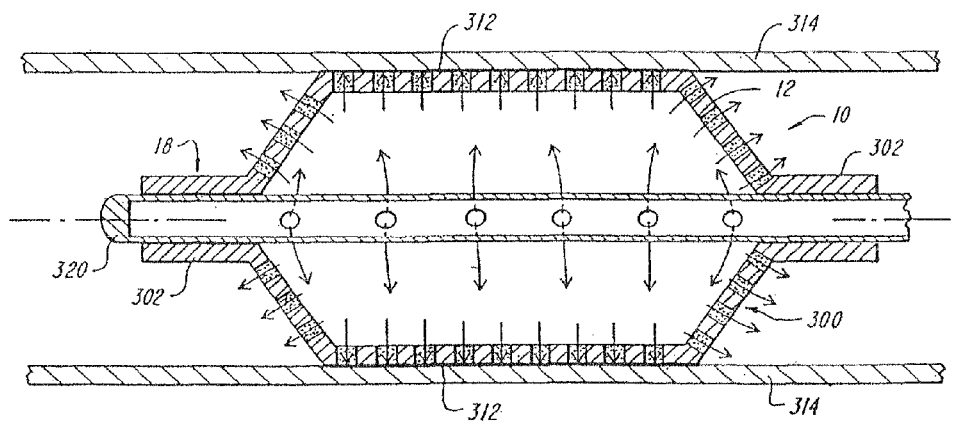
FIG. 12 is a side-elevational view in cross-section of a catheter deployed infusion balloon according to the teachings of the present invention, illustrating the infusion balloon expanded within a body vessel.

FIG. 12 illustrates an exemplary embodiment of the fluid delivery device of the present invention in which the fluid delivery device 10 of FIG. 1 is utilized as a catheter deployed dilation and diffusion balloon 300 for the treatment of a blood vessel 310 partially occluded by plaque deposits 312 adhered to the walls 314 of the blood vessel. This procedure is generally referred to as a Percutaneous Transluminal Angioplasty (PTA) procedure. The balloon 300 can be manufactured in accordance with the methods of the present invention and is shown in the expanded configuration. The ends 302 of the dilation balloon 300 are bonded to a catheter tube 320, which is used to provide an inflation fluid to the balloon 300 to effect expansion of the balloon 300 to a predefined and fixed maximum diameter. A therapeutic agent, such as antisense oligonucleotides (AS-ODNs), can be delivered through the walls of the balloon with the inflation fluid. The AS-ODNs are delivered locally to the walls of the body vessel to suppress restenosis of the PTA roc vessel subsequent to the PTA procedure.

A variety of therapeutic agents can be delivered with the fluid delivery device of the present invention. Exemplary therapeutic agents include: thrombolytics, antibiotics, chemotherapeutics, surfactants, diagnostic agents, steroids, hot saline, vasodilators, vasoconstrictors, and embolic agents. The localized delivery of thrombolytics, such as heparin, and urokinase, directly to the surface of thrombosed grafts or native body vessels can inhibit the-clotting of the graphs or native body vessels. The fluid delivery device of the present invention thus can be used as thrombolectomy balloon catheter to remove obstructions from grafts or native body vessels while concomitantly delivering thrombolytics to the walls of the graft or native body vessel.

The fluid delivery device of the present invention can further be used for the localized delivery of high concentrations of antibiotics to treatment sites such as the ear canal, the throat, and the upper respiratory passages. Anti-cancer agents such as chemotherapeutics delivered using the fluid delivery device of the present invention can increase the effectiveness and negate the systemic side effects of the anti-cancer agents. Exemplary forms of cancer targeted for this application can include: rectal, esophageal, and lung cancer. Surfactants can be delivered directly to the lungs using the fluid delivery device of the present invention to treat cystic fibrosis or hyaline membrane disease. Diagnostic agents can be delivered during angiography procedures through the fluid delivery device of the present invention to improve the visibility of contrast agents delivered locally to the treatment site. The local delivery of steroids, such as anabolic steroids, using the fluid delivery device of the present invention can increase the effectiveness, e.g., promote muscle recovery, and negate systemic side effects such as lung and adrenal gland vantage.

The fluid delivery device of the present invention can also be provided with hydrophilic or hydrophobic coatings dependant on the particular treatment applications. For example, fluid delivery devices constructed of ePTFE, a naturally hydrophobic material, can be coated with a hydrophilic coating to provide the fluid delivery device with a hydrophilic outer surface. A suitable hydrophilic coating is PHOTOLINK available from Surmodics of Eden Prairie, Minn.

Figure 15:
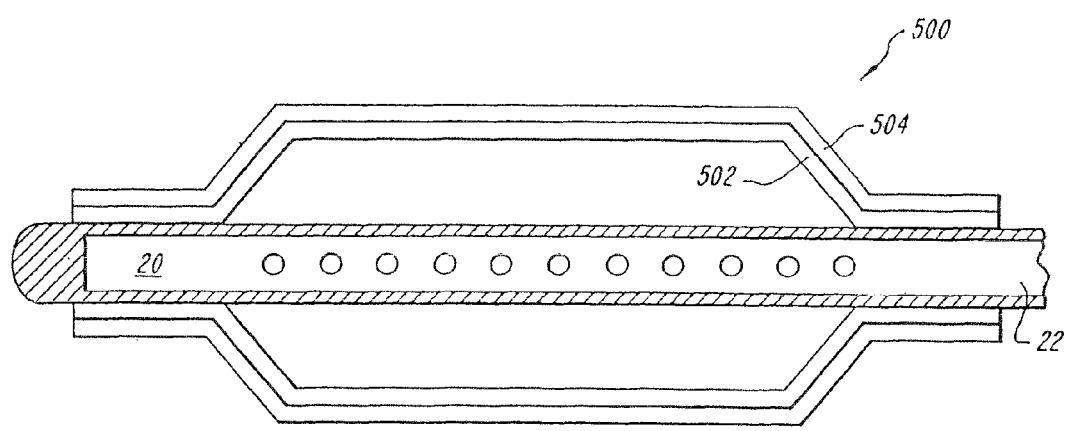
FIG. 15 is a side elevational view in cross-section of a multi-layer radially expandable fluid delivery device in accordance with the present invention, illustrating the device in a second, increased diameter configuration.

In an alternative embodiment illustrated in FIG. 15, the fluid delivery device of the present invention can be provided with multiple layers. The multi-layer fluid delivery device 500 includes a first layer 502 of biocompatible material, such as ePTFE, and a second layer 504 of biocompatible material that overlies the first layer 502. The second layer 504 can be constructed from the same or a different biocmopatible material than the first layer 502. As shown in FIG. 15, the first layer 502 and the second layer 504 are preferably coexentsive, however, the second layer 504 need not extend the entire length of the first layer 502. Likewise, the first layer 502 may be smaller in length than the second layer 504.

The first layer 502 and the second layer 504 can each be formed from a separate ePTFE tube. The ePTFE tubes can be constructed in accordance with the manufacturing methods of the present invention such that each tube is characterized by a microstructure of nodes interconnected by fibrils. Preferably the nodes are oriented generally perpendicular to the longitudinal axis. The two ePTFE tubes can then be coaxially disposed and heated to bond the two tubes together. The bonded tubes can be radially expanded by a balloon in accordance with the above manufacturing methods of the present invention. By producing the ePTFE tubes forming the first and second layers using different process parameters, e.g. different stretch ratios or stretch rates, the distance between the nodes can varied between the ePTFE tubes. For example, the internodal distances of the microstructure of the first layer 502 can be generally greater than the internodal distances of the microstructure of the second layer 504. In this manner, the porosity of the first layer 502 and the porosity of the second layer 504 can be different.

Although the multi-layer fluid delivery device 500 illustrated in FIG. 15 includes two layers, additional layers can be provided. Additional layers can be formed from further ePTFE tubes or through other methods, such as by wrapping ePTFE film about the first layer and/or second layer.

EXAMPLE 1

Figure 14A:
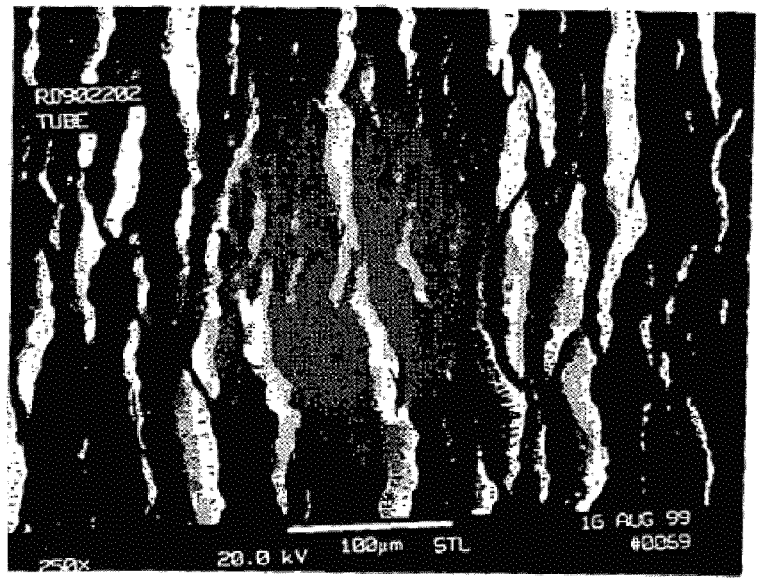
FIG. 14A is an electron micrograph of an external section of an ePTFE tube used in the manufacture of the fluid delivery device of the present invention.

An exemplary fluid delivery device was constructed according to the manufacturing processes of the present invention by employing 0.068" (ID)/0.088" (OD) ePTFE tubing. The longitudinal stretch ratio of the ePTFE tube was 1.5:1, at a stretch rate of 10 inches per second. An electron micrograph of an exterior section of a sample ePTFE tube, after stretching, is shown in FIG. 14A. FIG. 14A illustrates the microstructure of nodes interconnected by fibrils of the ePTFE tubing and, in particular, the orientation of the nodes generally perpendicular to the longitudinal axis of the tubing and the internodal through-pores. An 8 mm×8 cm PET balloon was employed to radially expand the ePTFE tubing. The PET balloon was attached to a vacuum source and a slight vacuum was placed on the PET balloon, about −5 to −10 psi. The ePTFE tubing was then positioned over the deflated PET balloon. The PET balloon and the ePTFE tubing were then connected to a hypo-tube and placed into a water heated chamber. Saline was injected into the PET balloon at a constant flow rate of about 10-15 ml/min. When the pressure within the balloon reached 70-80% of the rated balloon pressure, about 12-15 atm for the PET balloon employed, the flow rate was decreased to 2 ml/min. The balloon was then brought to its rated balloon pressure. The water was then removed from the PET balloon using the pump until a slight vacuum existed within the PET balloon (−5 to −10 psi). The hypo-tube was then removed from the chamber and the ePTFE tube was withdrawn from the balloon. The proximal I.D. of the resultant ePTFE tube was approximately ⅔ Fr larger than the distal I.D.

The resultant ePTFE balloon was then allowed to completely dry. The ePTFE balloon was cut to a desired length and the proximal tail of the ePTFE balloon was dipped into Loctite 7701 Prism Primer, available from Loctite, Corp. of Rocky Hill, Conn. The distal tail of the ePTFE balloon was then dipped into the primer. The primer was allowed to evaporate for at least two minutes. The ePTFE balloon was then placed on a 5 Fr-4 Fr tipped catheter by pulling the proximal end of the ePTFE balloon onto the 5 Fr end of the catheter body until the distal (4 Fr) end is about 0.1" from the tip of the catheter. The location of the proximal tail of the ePTFE balloon was then marked on the catheter and the ePTFE balloon was removed from the catheter. Loctite 4011 adhesive was then applied to the catheter shaft at a location slightly distal to the marked position. The ePTFE balloon was then slid back onto the catheter shaft until the proximal end was aligned with the mark. The adhesive was allowed to dry for one minute. A small volume of Loctite 4011 adhesive was dispensed onto the distal end of the catheter shaft adjacent to the distal end of the ePTFE balloon. This adhesive was drawn into the gap between the catheter and the balloon by capillary forces. The adhesive was then allowed to dry for at 24 hours.

Figure 14B:
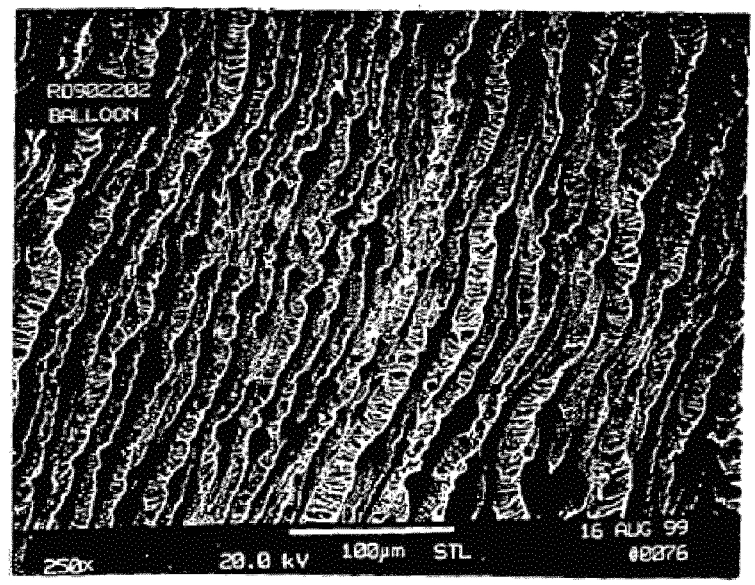
FIG. 14B is an electron micrograph of an external section of a fluid delivery device of the present invention.
Figure 14C:
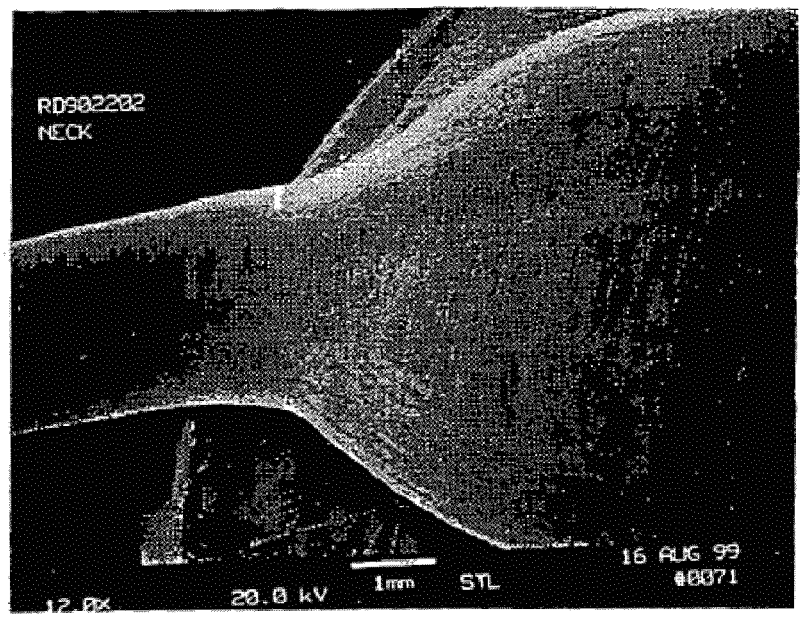
FIG. 14C-14D are electron micrographs of an external section of the neck of the fluid delivery device of FIG. 14B.
Figure 14D:
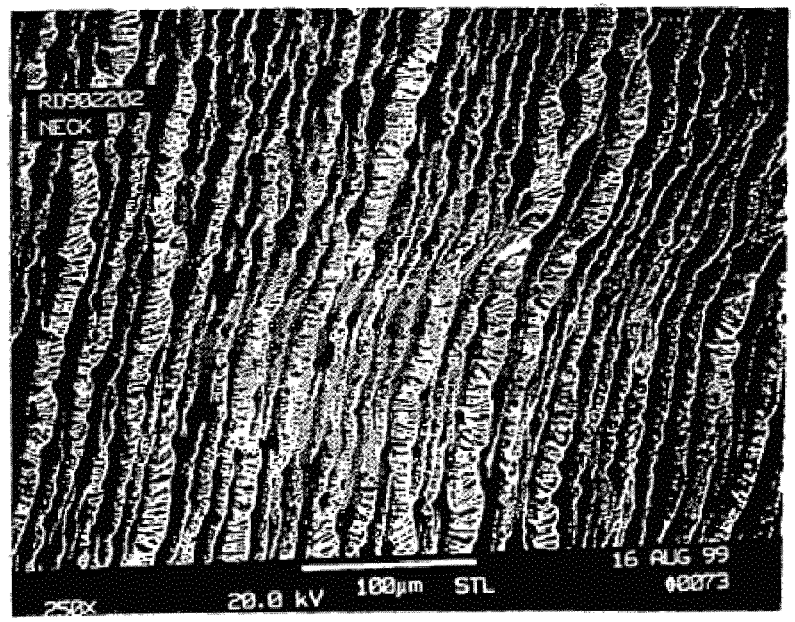

An electron micrograph of an exterior section of a sample ePTFE balloon is shown in FIGS. 14B-14D. FIG. 14B illustrates the microstructure of nodes interconnected by fibrils of the body of the ePTFE balloon. FIGS. 14C and 14D are cross-sections of the neck of the ePTFE balloon at varying magnifications. FIGS. 14B-14D illustrate the internodal through-pores or channels of the ePTFE balloon as defined by the microfibrillar spaces between the nodes. The through-pores are oriented generally perpendicular to the longitudinal axis of the ePTFE balloon and provide fluid pathways between the inner surface and the outer surface of the ePTFE balloon.

EXAMPLE 2

Three ePTFE synthetic grafts were treated using an ePTFE diffusion balloon constructed in accordance with the method of Example 1 to determine the permeability of a contrast agent into the grafts. The diffusion balloon employed was 8 cm in length, had an OD of 6 mm and was constructed from an 0.088" (OD)/0.068" (ID) ePTFE tube having a stretch ratio of 1.5:1. Each of the grafts treated was an Atrium Hybrid PTFE graft, model no. 01200670, available from Atrium Medical of Hudson, N.H. The grafts had a 6 mm inner diameter and a wall thickness of 0.025 inches. In each case, the balloon was inserted into a graft and inflated by infusing a contrast agent. The balloon was inflated to 1 atm. by the infused fluid. The balloon was then removed from the graft and the graft was flushed with water delivered at 500 ml/min. The contrast agent used was Hypaque-76 available from Mycomed, Inc. Table 1 summarizes each procedure.

TABLE 1

| Graft Sample | Duration of Balloon Infusion | Balloon Infusion Fluid | Graft Flushing Duration |
|---|---|---|---|
| 1 | 15 seconds | Saline & Contrast Agent | 5 minutes |
| 2 | 15 seconds | Saline & Contrast Agent | 30 seconds |
| 3 (Control) | 15 seconds | Saline | No Flushing |

X-rays were taken of each of the grafts samples to determine if the contrast agent was present in the grafts post infusion and perfusion (flushing). Table 2 summarizes the results of the X-rays for each graft.

TABLE 2

| Graft Sample | Presence of Contrast Agent |
|---|---|
| 1 | Yes |
| 2 | Yes |
| 3 | No |

Contrast agent was found in the walls of the both ePTFE graft samples infused with contrast agent by the diffusion balloon of the present invention, but not in the control sample. In graft samples 1 and 2, the contrast agent was found to have permeated through the entire wall of the graft. Flushing the grafts with water post infusion was determined to have no effect on the presence and concentration of the delivered contrast agent.

EXAMPLE 3

The permeability of several ePTFE fluid delivery devices constructed in accordance with the manufacturing processes of the present invention was evaluated and compared with the permeability of selected synthetic grafts. Each of the fluid delivery devices was constructed from an extruded and expanded ePTFE tube as set forth in Table 3.

TABLE 3

| Fluid Delivery Device Sample | Stretch Ratio of ePTFE tube | Stretch Rate of ePTFE tube (in/s) | Wall Thickness of Fluid Delivery Device (in) | Surface Area of Fluid Delivery Device (in$^2$) |
|---|---|---|---|---|
| 1 | 1.5:1 | 20 | 0.0068 | 0.456 |
| 2 | 1.75:1 | 10 | 0.0055 | 0.469 |
| 3 | 3:1 | 10 | 0.005 | 0.469 |
| 4 | 5.1 | 10 | 0.003 | 0.503 |
| 5 | 125:1 | 10 | 0.0075 | 0.399 |
| 6 | 1.5:1 | 0.5 | 0.0055 | 0.399 |
| 7 | 1.5:1 | 10 | 0.005 | 0.399 |
| 8 | 1.5:1 | 10 | 0.005 | 0.29 |

The synthetic grafts analyzed were standard and thin wall grafts available from Atrium Medical. Corporation and W. L. Gore & Associates, Inc. Information regarding the grafts is set forth in Table 4

TABLE 4

| Graft sample | Type | Wall Thickness (in) | Surface Area (in$^2$) |
|---|---|---|---|
| A | Atrium 6 mm std | 0.025 | 0.964 |
| B | Atrium 6 mm thin | 0.022 | 0.963 |
| C | Gore 7 mm thin | 0.016 | 1.143 |
| D | Gore 6 mm std | 0.024 | 0.963 |

TABLE 4-continued

| Graft sample | Type | Wall Thickness (in) | Surface Area (in$^2$) |
|---|---|---|---|
| E | Gore 4 mm | 0.025 | 0.59 |
| F | Atrium 4 mm | 0.02 | 0.49 |

The fluid delivery devices and the synthetic grafts were infused with a fluid to determine the permeability of the samples. The permeability of each of the samples is reflected by the hydrodynamic resistance and the hydraulic conductivity data set forth in Table 5.

TABLE 5

| Sample | Hydrodynamic resistance (psi * min * mL$^{-1}$) | Hydraulic Conductivity (cm$^4$/(dyne* s) * 10$^{12}$) |
|---|---|---|
| 1 | 21.2 | 67 |
| 2 | 7.18 | 155 |
| 3 | 2.76 | 368 |
| 4 | 2.81 | 202 |
| 5 | 13.4 | 134 |
| 6 | 1.59 | 825 |
| 7 | 1.5 | 795 |
| 8 | 1.7 | 966 |
| A | 2.394 | 1031 |
| B | 1.03 | 2112 |
| C | 0.711 | 1874 |
| D | 0.623 | 3808 |
| E | 1.5 | 2673 |
| F | 1.2 | 3207 |

Hydraulic conductivity was determined using Darcy's Law for describing steady flow through a porous media. Darcy's law is defined in Equation 1 as $$Q/A = -K(\Delta P/\Delta X), \quad \text{(Eq. 1)}$$

where Q is flow rate, A is cross sectional area for flow, i.e. the surface area of the sample, P is pressure, X is wall thickness, and K is the hydraulic conductivity.

Applicants determined that the permeability of a fluid delivery device relative to the permeability of the vessel being treated is an important consideration in establishing effective fluid delivery into the walls of the vessel. In particular, for a given fluid flow rate and pressure, a greater volume of fluid will penetrate the walls of a vessel being treated if the permeability of the vessel is greater than the permeability of the fluid delivery device. Accordingly, it is desirable for the permeability of the fluid delivery device to be less than the permeability of the vessel being treated. The permeability of the fluid delivery device can be tailored to be less than the vessel being treated by varying the process parameters of the manufacturing processes described above. The process parameters include lubricant density, lubricant viscosity, lubricant molecular weight, longitudinal stretch ratio, and stretch rate.

The permeability data set forth in Table 5 illustrates that the permeability, when measured in terms of the hydraulic conductivity, for each of the fluid delivery devices tested was less than the permeability of each of the synthetic grafts tested. This indicates that the Applicants' fluid delivery device may be particularly effective for delivering fluid to the walls of synthetic grafts.

Applicants have determined that it is desirable for the hydraulic conductivity of the fluid delivery device to be less than 1000 (cm$^4$/(dyne*s)*10$^{12}$) for treatment of synthetic grafts. Preferably, the fluid delivery device has a hydraulic conductivity of less than 500 (cm$^4$/(dyne*s)*10$^{12}$). For treatment of natural body vessels and grafts, it is preferable for the hydraulic conductivity of the fluid delivery device to be less than 100 (cm$^4$/(dyne*s)*10$^{12}$).

It will thus be seen that the invention efficiently attains the objects made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and desired to be secured by Letters Patent is:

1. A method of using a radially expandable fluid delivery device for delivery of one or more therapeutic agents, comprising:
   locating the radially expandable fluid delivery device within a body passage in need of treatment, the radially expandable fluid delivery device formed of a radially inelastic wall having at least one microporous portion formed of a microstructure of nodes interconnected by fibrils having spaces therebetween forming generally aligned micro-channels having a porosity sufficient to cause a fluid containing the one or more therapeutic agents and supplied thereto to provide a radial deployment force to expand the fluid delivery device and to permeate through the micro-channels, the micro-channels substantially controlling the permeation of the fluid from a location interior to the wall to a location exterior to the wall by passing through the wall; and
   expanding the radially expandable fluid delivery device using a radial deployment force supplied by the fluid containing the one or more therapeutic agents in such a way that the radially expandable fluid delivery device expands and occludes the body passage and the fluid containing the one or more therapeutic agents flows from the location interior to the wall to the location exterior to the wall by flowing through the wall of the radially expandable fluid delivery device thereby delivering the one or more therapeutic agents to the body passage while also applying the radial deployment force.

2. The method of claim 1, wherein the radially expandable fluid delivery device is made of biocompatible material, and wherein the radially inelastic wall is unitary and seamless.

3. The method of claim 1, wherein the nodes are separated by an internodal distance of about 1 μm to 150 μm.

4. The method of claim 1, wherein expanding the radially expandable fluid delivery device comprises providing the fluid at a pressure of between about 1 psi to 250 psi.

5. The method of claim 1, wherein the wall of the radially expandable fluid delivery device has a porosity sufficient to allow fluid to pass therethrough at a flow rate of about 0.01 ml/min to 100 ml/min.

6. The method of claim 1, wherein the one or more therapeutic agents comprise thrombolytics, antibiotics, antisense oligonucleotides, chemotherapeutics, surfactants, diagnostic agents, steroids, vasodilators, vasoconstrictors, or embolic agents.

7. The method of claim 1, wherein the one or more therapeutic agents comprise heparin and/or urokinase.

8. The method of claim 1, wherein expanding the radially expandable fluid delivery device and delivering the one or more therapeutic agents occurs simultaneously and by a single radially expandable fluid delivery device.

9. The method of claim 1, wherein delivering the one or more therapeutic agents occurs in such a way as to reduce the volume of the one or more therapeutic agents delivered to a periphery of the body passage in need of treatment to minimize damage to healthy tissue located away from the body passage in need of treatment.

10. The method of claim 1, wherein delivering the one or more therapeutic agents occurs in such a way as to deliver relatively high concentrations of the one or more therapeutic agents to localized areas of the body passage in need of treatment.

11. The method of claim 1, wherein delivering the one or more therapeutic agents occurs using relatively high concentrations of the one or more therapeutic agents to localized areas of the body passage in need of treatment in such a way as to increase effectiveness of the one or more therapeutic agents and negate systemic side effects from the one or more therapeutic agents.

12. A method of using a radially expandable fluid delivery device for delivery of one or more therapeutic agents, comprising:
   locating the radially expandable fluid delivery device at a body location, the radially expandable fluid delivery device formed of a radially inelastic wall having at least one microporous portion formed of a microstructure of nodes interconnected by fibrils having spaces therebetween forming generally aligned micro-channels having a porosity sufficient to cause a fluid containing the one or more therapeutic agents and supplied thereto to provide a radial deployment force to expand the fluid delivery device and to permeate through the micro-channels, the micro-channels substantially controlling the permeation of the fluid through the wall, the method; and
   expanding the radially expandable fluid delivery device using a radial deployment force supplied by the fluid containing the one or more therapeutic agents in such a way that the fluid containing the one or more therapeutic agents flows from a location interior to the wall to a location exterior to the wall by flowing through the wall of the radially expandable fluid delivery device thereby delivering the one or more therapeutic agents to the body location.

13. The method of claim 12, wherein the body location comprises multiple sites within the body that are treated.

14. The method of claim 12, wherein the radially expandable fluid delivery device is made of biocompatible material, and wherein the radially inelastic wall is unitary and seamless.

15. The method of claim 12, wherein the nodes are separated by an internodal distance of about 1 μm to 150 μm.

16. The method of claim 12, wherein expanding the radially expandable fluid delivery device comprises providing the fluid at a pressure of between about 1 psi to 250 psi.

17. The method of claim 12, wherein the wall of the radially expandable fluid delivery device has a porosity sufficient to allow fluid to pass therethrough at a flow rate of about 0.01 ml/min to 100 ml/min.

18. The method of claim 12, wherein the one or more therapeutic agents comprise thrombolytics, antibiotics, antisense oligonucleotides, chemotherapeutics, surfactants, diagnostic agents, steroids, vasodilators, vasoconstrictors, or embolic agents.

19. The method of claim 12, wherein the one or more therapeutic agents comprise heparin and/or urokinase.

20. The method of claim 12, wherein expanding the radially expandable fluid delivery device and delivering the one or more therapeutic agents occurs simultaneously and by a single radially expandable fluid delivery device.

21. The method of claim 12, wherein delivering the one or more therapeutic agents occurs in such a way as to reduce the volume of the one or more therapeutic agents delivered to a periphery of the body location to minimize damage to healthy tissue located away from the body location.

22. The method of claim 12, wherein delivering the one or more therapeutic agents occurs in such a way as to deliver relatively high concentrations of the one or more therapeutic agents to localized areas of the body location.

23. The method of claim 12, wherein delivering the one or more therapeutic agents occurs using relatively high concentrations of the one or more therapeutic agents to localized areas of the body location in such a way as to increase effectiveness of the one or more therapeutic agents and negate systemic side effects from the one or more therapeutic agents.

24. A method of using a radially expandable fluid delivery device for delivery of one or more therapeutic agents, comprising:

locating the radially expandable fluid delivery device within a body passage in need of treatment, the radially expandable fluid delivery device formed of a unitary, seamless and radially inelastic wall comprised of an expanded fluoropolymer, the radially inelastic wall constructed to be tubular and having a distal portion and a proximal portion, the wall having at least one microporous portion formed of a microstructure of nodes interconnected by fibrils having spaces therebetween forming generally aligned micro-channels having a porosity sufficient to cause a fluid containing the one or more therapeutic agents and supplied thereto to provide a radial deployment force to expand the fluid delivery device and to permeate through the micro-channels, the micro-channels substantially controlling the permeation of the fluid outwardly from a location interior to the radially inelastic wall to a location exterior to the radially inelastic wall by passing through the radially inelastic wall, the radially expandable fluid delivery device further comprising a catheter having a sidewall and extending from a proximal end of the radially inelastic wall to a distal end of the radially inelastic wall, at least one aperture in the catheter's sidewall for establishing fluid communication between the catheter and the location interior to the radially inelastic wall; and expanding the radially expandable fluid delivery device using a radial deployment force supplied by the fluid containing the one or more therapeutic agents in such a way that the radially expandable fluid delivery device expands and occludes the body passage and the fluid containing the one or more therapeutic agents flows from the location interior to the wall to the location exterior to the wall by flowing through the radially inelastic wall of the radially expandable fluid delivery device thereby delivering the one or more therapeutic agents to the body passage while also applying the radial deployment force.

\* \* \* \* \*